United States Patent [19]

Shah et al.

[11] Patent Number: 5,188,642
[45] Date of Patent: * Feb. 23, 1993

[54] GLYPHOSATE-RESISTANT PLANTS

[75] Inventors: Dilip M. Shah, Creve Coeur, Mo.; Stephen G. Rogers, Brussels, Belgium; Robert B. Horsch, St. Louis, Mo.; Robert T. Fraley, St. Louis, Mo.

[73] Assignee: Monsanto Company, St. Louis, Mo.

[*] Notice: The portion of the term of this patent subsequent to Jul. 10, 2007 has been disclaimed.

[21] Appl. No.: 478,794

[22] Filed: Feb. 12, 1990

Related U.S. Application Data

[63] Continuation-in-part of Ser. No. 879,814, Jul. 7, 1986, Pat. No. 4,940,835, which is a continuation-in-part of Ser. No. 792,390, Oct. 29, 1985, abandoned, which is a continuation-in-part of Ser. No. 763,482, Aug. 7, 1985, abandoned.

[51] Int. Cl.⁵ .................. A01H 1/00; A01H 5/10; C12P 21/00; C12P 21/04; C12N 15/00; C12N 9/00; A01N 57/00
[52] U.S. Cl. .................. 47/58; 435/69.1; 435/69.7; 435/69.8; 435/70.1; 435/172.3; 435/183; 800/205; 800/255; 800/DIG. 14; 800/DIG. 17; 800/DIG. 24; 800/DIG. 26; 800/DIG. 27; 800/DIG. 43; 800/DIG. 44; 935/35; 935/48; 935/67; 935/64; 504/206; 504/205; 504/195; 504/197; 504/117
[58] Field of Search ........... 435/69.1, 172.3, 183, 435/69.7, 69.8, 70.1; 800/205, 255, DIG. 14, DIG. 17, DIG. 24, DIG. 26, DIG. 27, DIG. 43, DIG. 44; 71/86; 47/58; 935/35, 48, 67, 64

[56] References Cited

U.S. PATENT DOCUMENTS 4,940,835  7/1990  Shah et al. .................. 800/205

Primary Examiner—David T. Fox
Attorney, Agent, or Firm—Dennis R. Hoerner, Jr.; Howard C. Stanley

[57] ABSTRACT

This invention involves a cloning or expression vector comprising a gene which encodes 5-enolpyruvylshikimate-3-phosphate synthase (EPSPS) polypeptide which, when expressed in a plant cell contains a chloroplast transit peptide which allows the polypeptide, or an enzymatically active portion thereof, to be transported from the cytoplasm of the plant cell into a chloroplast in the plant cell, and confers a substantial degree of glyphosate resistance upon the plant cell and plants regenerated therefrom.

The EPSPS coding sequence may be ligated to a strong promoter, such as the 35S promoter from cauliflower mosaic virus, to create a chimeric gene. Such genes can be inserted into plant transformation vectors, and subsequently introduced into plant cells. Plant cells transformed using such genes and plants regenerated therefrom have been shown to exhibit a substantial degree of glyphosate resistance.

23 Claims, 13 Drawing Sheets

```
1    GAATTCCCTCAATCTTTACTTTCAAGAATGGCACAAATTAACAACATGGCACAAGGGATA    60
                                 MetAlaGlnIleAsnAsnMetAlaGlnGlyIle

61   CAAACCCTTAATCCCCAATTCCAATTTCCATAAACCCCAAGTTCCTAAATCTTCAAGTTT    120
     GlnThrLeuAsnProAsnSerAsnPheHisLysProGlnValProLysSerSerPhe

121  CTTGTTTTTGGGATCTAAAAAACTGAAAAAATTCAGCAAATTCTATGTTGGTTTTGAAAAA    180
     LeuValPheGlySerLysLysLeuLysLysAsnSerAlaAsnSerMetLeuValLeuLysLys

181  GATTCAATTTTATGCAAAAGTTTTGTTCCTTTAGGATTTCAGCATCAGTGGCTACAGCA    240
     AspSerIlePheMetGlnLysPheCysSerPheArgIleSerAlaSerValAlaThrAla

241  CAG
     Gln
```

FIG. 3

| | | |
|---|---|---|
| 1 | GAATTCCCTCAATCTTTACTTTCAAGAATGGCACAAATTAACAACATGGCTCAAGGGATA<br>                        MetAlaGlnIleAsnAsnMetAlaGlnGlyIle | 60 |
| 61 | CAAACCCTTAATCCCAATTCCAATTTCCATAAACCCCAAGTTCCTAAATCTTCAAGTTTT<br>GlnThrLeuAsnProAsnSerAsnPheHisLysProGlnValProLysSerSerSerPhe | 120 |
| 121 | CTTGTTTTTGGATCTAAAAAACTGAAAAATTCAGCAAATTCTATGTTGGTTTTGAAAAAA<br>LeuValPheGlySerLysLysLeuLysAsnSerAlaAsnSerMetLeuValLeuLysLys | 180 |
| 181 | GATTCAATTTTTATGCAAAAGTTTTGTTCCTTTAGGATTTCAGCATCAGTGGCTACAGCA<br>AspSerIlePheMetGlnLysPheCysSerPheArgIleSerAlaSerValAlaThrAla<br>   \|---->matureEPSPS | 240 |
| 241 | CAGAAGCCTTCTGAGATAGTGTTGCAACCCATTAAAGAGATTTCAGGCACTGTTAAATTG<br>GlnLysProSerGluIleValLeuGlnProIleLysGluIleSerGlyThrValLysLeu | 300 |
| 301 | CCTGGCTCTAAATCATTATCTAATAGAATTCTCCTTCTTGCTGCCTTATCTGAAGGAACA<br>ProGlySerLysSerLeuSerAsnArgIleLeuLeuLeuAlaAlaLeuSerGluGlyThr | 360 |
| 361 | ACTGTGGTTGACAATTTACTAAGTAGTGATGATATTCATTACATGCTTGGTGCCTTGAAA<br>ThrValValAspAsnLeuLeuSerSerAspAspIleHisTyrMetLeuGlyAlaLeuLys | 420 |
| 421 | ACACTTGGACTGCATGTAGAAGAAGATAGTGCAAACCAACGAGCTGTTGTTGAAGGTTGT<br>ThrLeuGlyLeuHisValGluGluAspSerAlaAsnGlnArgAlaValValGluGlyCys | 480 |
| 481 | GGTGGGCTTTTCCCTGTTGGTAAAGAGTCCAAGGAAGAAATTCAACTGTTCCTTGGAAAT<br>GlyGlyLeuPheProValGlyLysGluSerLysGluGluIleGlnLeuPheLeuGlyAsn | 540 |
| 541 | GCAGGAACAGCAATGCGGCCACTAACAGCAGCAGTTACTGTAGCTGGTGGAAATTCAAGG<br>AlaGlyThrAlaMetArgProLeuThrAlaAlaValThrValAlaGlyGlyAsnSerArg | 600 |
| 601 | TATGTACTTGATGGAGTTCCTCGAATGAGAGAGAGACCAATTAGTGATTTGGTTGATGGT<br>TyrValLeuAspGlyValProArgMetArgGluArgProIleSerAspLeuValAspGly | 660 |
| 661 | CTTAAACAGCTTGGTGCAGAGGTTGATTGTTTCCTTGGTACGAAATGTCCTCCTGTTCGA<br>LeuLysGlnLeuGlyAlaGluValAspCysPheLeuGlyThrLysCysProProValArg | 720 |
| 721 | ATTGTCAGCAAGGGAGGTCTTCCTGGAGGGAAGGTCAAGCTCTCTGGATCCATTAGCAGC<br>IleValSerLysGlyGlyLeuProGlyGlyLysValLysLeuSerGlySerIleSerSer | 780 |
| 781 | CAATACTTGACTGCTCTGCTTATGGCTGCTCCACTGGCTTTAGGAGATGTGGAGATTGAA<br>GlnTyrLeuThrAlaLeuLeuMetAlaAlaProLeuAlaLeuGlyAspValGluIleGlu | 840 |
| 841 | ATCATTGACAAACTAATTAGTGTACCTTATGTCGAGATGACATTGAAGTTGATGGAGCGA<br>IleIleAspLysLeuIleSerValProTyrValGluMetThrLeuLysLeuMetGluArg | 900 |
| 901 | TTTGGTATTTCTGTGGAGCACAGTAGTAGCTGGGACAGGTTCTTTGTCCGAGGAGGTCAG<br>PheGlyIleSerValGluHisSerSerSerTrpAspArgPhePheValArgGlyGlyGln | 960 |
| 961 | AAATACAAGTCTCCTGGAAAAGCTTTTGTCGAAGGTGATGCTTCAAGTGCTAGCTACTTC<br>LysTyrLysSerProGlyLysAlaPheValGluGlyAspAlaSerSerAlaSerTyrPhe | 1020 |
| 1021 | TTGGCTGGTGCAGCAGTCACAGGTGGAACTATCACTGTTGAAGGTTGTGGGACAAACAGT<br>LeuAlaGlyAlaAlaValThrGlyGlyThrIleThrValGluGlyCysGlyThrAsnSer | 1080 |
| 1081 | TTACAGGGGGATGTCAAATTTGCTGAGGTACTTGAAAAAATGGGAGCTGAAGTTACGTGG<br>LeuGlnGlyAspValLysPheAlaGluValLeuGluLysMetGlyAlaGluValThrTrp | 1140 |

```
1141  ACAGAGAACAGTGTCACAGTCAAAGGACCTCCAAGGAGTTCTTCTGGGAGGAAGCATTTG        1200
      ThrGluAsnSerValThrValLysGlyProProArgSerSerSerGlyArgLysHisLeu

1201  CGTGCCATTGATGTGAACATGAATAAAATGCCTGATGTTGCCATGACACTTGCTGTTGTT        1260
      ArgAlaIleAspValAsnMetAsnLysMetProAspValAlaMetThrLeuAlaValVal

1261  GCACTTTATGCTGATGGTCCCACAGCTATAAGAGATGTTGCTAGCTGGAGAGTCAAGGAA        1320
      AlaLeuTyrAlaAspGlyProThrAlaIleArgAspValAlaSerTrpArgValLysGlu

1321  ACTGAGCGCATGATCGCCATATGCACAGAACTTAGGAAGTTAGGAGCAACCGTTGAAGAA        1380
      ThrGluArgMetIleAlaIleCysThrGluLeuArgLysLeuGlyAlaThrValGluGlu

1381  GGACCAGACTACTGCATAATCACCCCACCGGAGAAACTAAATGTGACCGATATTGATACA        1440
      GlyProAspTyrCysIleIleThrProProGluLysLeuAsnValThrAspIleAspThr

1441  TACGATGATCACAGGAATGCCATGGCTTTTTCTCTTGCTGCTTGTGCAGATGTTCCCGTC        1500
      TyrAspAspHisArgAsnAlaMetAlaPheSerLeuAlaAlaCysAlaAspValProVal

1501  ACCATCAATGACCCTGGCTGCACGCGGAAAACCTTCCCTAACTACTTTGATGTACTTCAG        1560
      ThrIleAsnAspProGlyCysThrArgLysThrPheProAsnTyrPheAspValLeuGln

1561  CAGTACTCCAAGCATTGAACCGCTTCCCTATATTGCAGAATGTAAGTAAGAATATGTGAA        1620
      GlntyrSerLysHisEnd

1621  GAGTTTAGTTCTTGTACAAGACAGGCTACGACTGCCTGGTATCAGAACCACAATGGGTTC        1680

1681  CATTTCAGTTCAGAAGGGCATTCCAAGGCTTCGAACTCTTTACTTATTTGCGAGTGATGA        1740

1741  AATGTATTTGTTAGAGTTGAGCTTCTTTTTGTCTTTAAGGAATGTACACTAATAGAGTTA        1800

1801  AGAATTACTAGTATGGGCCAGTGTAAGGAGTACTATTACTCTTTGCTTATTTTATTGATT        1860

1861  GAGTTTTGTCAAGGATCTGGCTTTGTCAAGAATTACTGGTTAATTTTATTGACAATCTCA        1920

1921  TGTGTCTAAATGAAATTGTTTGATAAAAAAAAAAAAAAAAAAAAAAAAAAAGGAATTC         1976
```

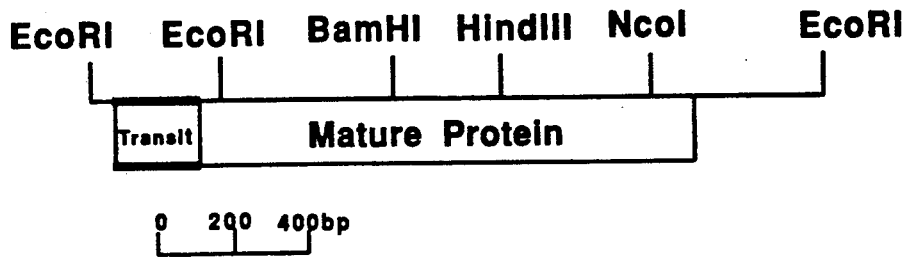

FIGURE 4(2 of 2)

GLYPHOSATE-RESISTANT PLANTS

This application is a continuation-in-part application of and claims priority from our copending application Ser. No. 06/879,814, filed Jul. 7, 1989 now U.S. Pat. No. 4,940,835, which is a continuation-in-part of application Ser. No. 792,390, filed Oct. 29, 1985 abandoned, which, in turn, is a continuation-in-part of application Ser. No. 763,482, filed Aug. 7, 1985 abandoned.

BACKGROUND OF THE INVENTION

The present invention relates to the fields of genetic engineering, biochemistry, and plant biology.

N-phosphonomethylglycine has the following structure:

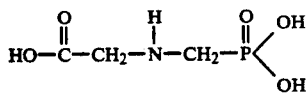

This molecule is an acid, which can dissociate in aqueous solution to form phytotoxicant anions. Several anionic forms are known. As used herein, the name "glyphosate" refers to the acid and its anions. A mixture containing glyphosate as the active ingredient, formulated as its isopropylamine salt, is sold as a herbicide by Monsanto Company under the trademark ROUNDUP®. Numerous other salts also have herbicidal properties, as exemplified by U.S. Pat. No. 3,799,758 (Franz 1974) and various other patents. Compositions comprising N-phosphonomethylglycine and salt-forming cations which increase the solubility of the N-phosphonomethylglycine in water are preferred.

Those skilled in the art recognize that the scientific literature contains numerous papers suggesting several modes of action for inhibition of plant growth by glyphosate. One proposed mode suggests that glyphosate inhibits an enzyme called 5-enolpyruvylshikimate-3-phosphate synthase (EPSPS); see, e.g., Amrhein 1980, Steinrucken 1980, Mousdale 1984, and Rubin 1982 (note: a complete list of references is contained below, after the Examples). The EPSPS enzyme reportedly catalyzes the conversion of shikimate-3-phosphate into 5-enolpyruvyl-shikimate-3-phosphate, an intermediate in the biochemical pathway for creating three essential aromatic amino acids (tyrosine, phenylalanine, and tryptophan); see, e.g., Mousdale 1984. Rogers 1983 reports that overproduction of EPSPS in *E. coli* contributes to glyphosate resistance in those cells.

At least one researcher has attempted to create glyphosate-resistant bacterial cells by manipulating a bacterial gene which encodes an EPSPS enzyme. As described in U.S. Pat. No. 4,535,060 (Comai; assigned to Calgene, Inc.; filing date Jan. 5, 1983) and in Comai 1983, a culture of Salmonella bacteria was contacted with a mutagen (ethyl methanesulfonate). The bacteria were screened for glyphosate resistance, and a relatively resistant culture was selected. This culture was analyzed, and determined to have a mutant form of EPSPS with a substituted amino acid, as reported in Stalker 1985. U.S. Pat. No. 4,535,060 suggested that the mutant EPSPS gene could be inserted into plant cells to create glyphosate-resistant ($Gly^R$) plant cells. In addition, it has been reported that glyphosate tolerant plant cells can be selected which overproduce EPSPS in the presence of low levels of glyphosate (Nafziger et al, 1984 and Smart et al, 1985). However, none of the experiments have demonstrated that such a method would be efficacious in differentiated plants. After the filing date of U.S. Pat. No. 4,535,060, methods and vectors were described which could be used to insert foreign genes into plant cells (see, e.g., Fraley 1983, Herrera-Estrella 1983, Bevan 1983, and PCT applications WO 84/02919 and 02920). In PCT application WO 84/02913, methods were also described for creating chimeric genes having bacterial EPSPS coding sequences controlled by regulatory sequences derived from genes which are active in plant cells. Using these vectors and methodology, bacterial genes such as the mutant Salmonella EPSPS gene mentioned above can be manipulated and expressed in plant cells.

The object of this invention is to provide a method of genetically transforming plant cells which causes the cells and plants regenerated therefrom to become resistant to glyphosate and the herbicidal salts thereof.

SUMMARY OF THE INVENTION

This invention involves a cloning or expression vector comprising a gene which encodes 5-enolpyruvylshikimate-3-phosphate synthase (EPSPS) polypeptide which, when expressed in a plant cell contains a chloroplast transit peptide which allows the polypeptide, or an enzymatically active portion thereof, to be transported from the cytoplasm of the plant cell into a chloroplast in the plant cell, and confers a substantial degree of glyphosate resistance upon the plant cell and plants regenerated therefrom.

This invention further involves dicotyledonous plants expressing a chimeric gene such that the plants exhibit resistance to glyphosate containing herbicides. The chimeric gene includes: a promoter sequence which functions in plant cells; a coding sequence which causes the production of RNA, encoding a chloroplast transit peptide/5-enolpyruvylshikimate-3-phosphate synthase fusion polypeptide, which chloroplast transit peptide permits the fusion polypeptide to be imported into a chloroplast of a plant cell; and a 3' non-translated region which encodes a polyadenylation signal which functions in plant cells to cause the addition of polyadenylate nucleotides to the 3' end of the RNA, where the promoter is heterologous with respect to the coding sequence and adapted to cause sufficient expression of the fusion polypeptide to enhance the glyphosate resistance of a plant cell transformed with said gene. As a result, a glyphosate-containing herbicide can be applied to a field where plants containing said chimeric gene are growing to selectively kill or control weeds that may also be growing in the field that are not glyphosate resistant. This allows the desired glyphosate resistant plants to take full advantage of the available nutrients in the field for an improved crop quality and yield.

This invention also involves seeds of dicotyledonous plants containing the chimeric gene including the coding sequence for the EPSPS polypeptide and the chloroplast transit peptide.

The EPSPS coding sequence may be ligated to a strong promoter, such as the 35S promoter from cauliflower mosaic virus, to create a chimeric gene. Such genes can be inserted into plant transformation vectors, and subsequently introduced into plant cells. Plant cells transformed using such genes and plants regenerated therefrom have been shown to exhibit a substantial degree of glyphosate resistance.

BRIEF DESCRIPTION OF THE DRAWINGS

FIG. 3 indicates the DNA sequence and the amino acid sequence of the chloroplast transit peptide from the petunia EPSPS gene and enzyme.

FIGS. 4a and 4b show the nucleotide, amino acid sequence and restriction map for the full-length cDNA of petunia EPSPS.

DETAILED DESCRIPTION OF THE INVENTION

Figure 1:
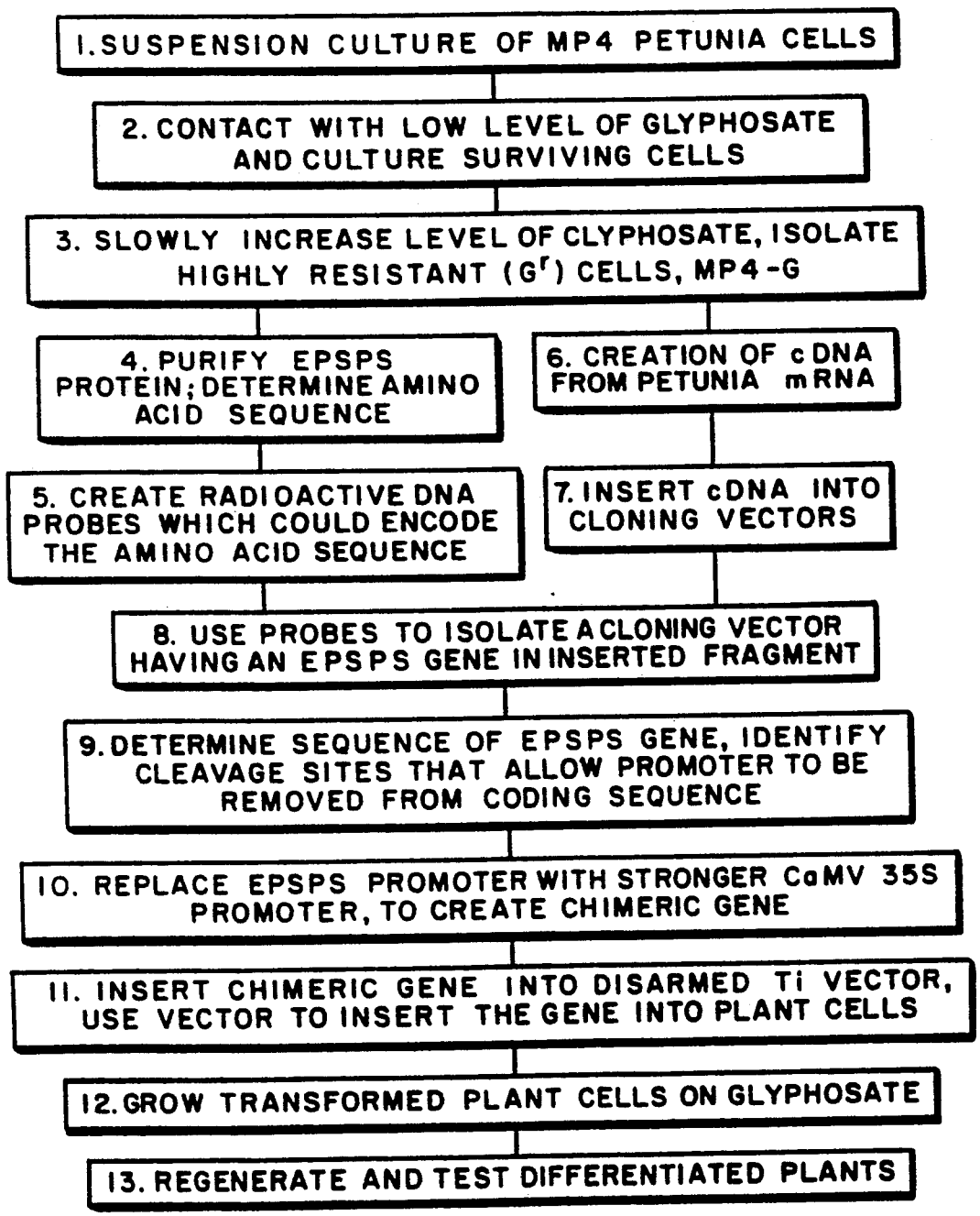
FIG. 1 depicts the major steps used in one preferred embodiment of this invention.

The present invention embraces a cloning or expression vector which contains a gene which encodes a form of EPSPS which can effectively confer glyphosate resistance (Gly$^R$) on plant cells and plants regenerated therefrom. The EPSPS gene encodes a polypeptide which contains a chloroplast transit peptide (CTP), which enables the EPSPS polypeptide (or an active portion thereof) to be transported into a chloro-plast inside the plant cell. Suitable plants for the practice of the present invention include, but are not limited to, soybean, cotton, alfalfa, canola, flax, tomato, sugar beet, sunflower, potato, tobacco, corn, wheat, rice and lettuce.

Those skilled in the art recognize that the scientific literature contains numerous papers stating that EPSPS activity (shikimic acid pathway) is present both in the chloroplast and in the cytoplasm. Indeed, prior to the present invention it was unknown whether the cloned EPSPS would be needed in the cytoplasm or chloroplasts in order to confer glyphosate resistance. Contrary to the teaching of U.S. Pat. No. 4,535,060 it has now been found that the EPSPS gene should contain a chloroplast transit peptide. While chloroplasts contain DNA which is believed to be expressed in polypeptides within the chloroplasts, the EPSPS polypeptide is encoded by chromosomal DNA rather than chloroplast DNA. The EPSPS gene is transcribed into mRNA in the nucleus and the mRNA is translated into a precusor polypeptide (CTP/mature EPSPS) in the cytoplasm. The precusor polypeptide (or a portion thereof) is transported into the chloroplast.

Promoters which are known or found to cause transcription of the EPSPS gene in plant cells can be used in the present invention. Such promoters may be obtained from plants or viruses and include, but are not necessarily limited to, the 35S and 19S promoters of cauliflower mosaic virus and promoters isolated from plant genes such as EPSPS, ssRUBISCO genes and promoters obtained from T-DNA genes of *Agrobacterium tumefaciens* such as nopaline and mannopine synthases. The particular promoter selected should be capable of causing sufficient expression to result in the production of an effective amount of EPSPS polypeptide to render the plant cells and plants regenerated therefrom substantially resistant to glyphosate. Those skilled in the art will recognize that the amount of EPSPS polypeptide needed to induce resistance may vary with the type of plant. The degree of expression needed may vary with the EPSPS coding sequence used. A mutant EPSPS may require lower expression than a less-tolerant wild-type EPSPS sequence.

The CaMV 35S promoter is stronger than the natural EPSPS promoter in at least some types of plants, i.e. it causes the formation of larger quantities of mRNA from chimeric genes compared to the natural EPSPS promoter. The high strength of the chimeric CaMV 35S/EPSPS gene is of great value in using the EPSPS gene as a selectable marker in the laboratory. However, when a chimeric gene is used to transform regenerated plants for food production, the level of production of EPSPS enzyme may be undesirably high, since it diverts nucleotides, amino acids, and substrates away from other desired biochemical pathways in the cells. Therefore, to create a chimeric gene with the optimal level of expression of EPSPS it may be desirable to diminish the strength of the chimeric CaMV 35S/EPSPS gene. This can be done by various methods such as (1) random or site-specific mutagenesis of the region prior to the transcription start site; (2) insertion of a transcription terminator in the 5' non-translated region of the gene; (3) insertion of a spurious start codon in front of the EPSPS start codon; or (4) insertion of a coding sequence with a start codon and a stop codon in front of the EPSPS start codon, to create a dicistronic coding sequence.

The promoters used in the EPSPS genes of this invention may be further modified if desired to alter their expression characteristics. For example, the CaMV 35S promoter may be ligated to the portion of the ssRUBISCO gene which represses the expression of ssRUBISCO in the absence of light, to create a promoter which is active in leaves but not in roots. The resulting chimeric promoter may be used as described herein. As used herein, the phrase "CaMV 35S" promoter includes variations of CaMV 35S promoter, e.g., promoters derived by means of ligation with operator regions, random or controlled mutagenesis, etc.

It is preferred that the endogenous EPSP synthase be expressed at high levels in the meristematic tissue of the plant. This can best be accomplished through use of a full-length promoter from the figwort mosaic virus or from a promoter that is capable of conferring high levels of expression in meristematic tissue, such as the meristematic promoter from *Arabidopsis thaliana*, described in Example 20. The full-length promoter from the figwort mosaic virus and the meristematic promoter are disclosed in the commonly assigned United States patent applications having U.S. Ser. Nos. 07/429,917 and 07/463,682, respectively, and filed on Oct. 31, 1989 and Jan. 11, 1990, respectively, the disclosures of which are hereby incorporated by reference.

The RNA produced by the EPSPS gene also contains a 5' non-translated leader sequence. This sequence may be derived from any gene and may be specifically modified so as to increase translation of the mRNA. The 5' non-translated regions may be derived from viral RNAs, other suitable eukaryotic genes or a synthetic gene sequence. It may be part of the 5' end of the non-translated region of the coding sequence for the EPSPS polypeptide or derived from an unrelated promoter or coding sequence as discussed above.

The EPSPS gene of the present invention encodes an CTP/EPSPS fusion polypeptide. After the CTP/EPSPS polypeptide from a gene of this invention is translated from mRNA in the cytoplasm of the transformed plant cell, it is believed to be processed in the same manner as the natural EPSPS polypeptide. The CTP leader sequence causes the polypeptide to be imported into chloroplasts, and the CTP leader sequence encoded by the plant-derived EPSPS gene is believed to be removed from the remainder of the polypeptide so that an active portion of the EPSPS polypeptide exists and functions inside the chloroplast.

Suitable CTP's for use in the present invention may be obtained from various sources. Most preferably, the CTP is obtained from the endogenous EPSPS gene of the subject plant to the transformed. Alternately, one may often use a CTP from an EPSPS gene of another plant. Although there is little homology between the CTP sequences of the EPSPS gene and the ssRUBISCO gene (see, e.g., Broglie (1983)), one may find that non-homologous CTPs may function in particular embodiments. Suitable CTP sequences for use in the present invention can be easily determined by assaying the chloroplast uptake of an EPSPS polypeptide comprising the CTP of interest as described in Example 18 hereinafter.

The sequence encoding a EPSPS polypeptide can be obtained from numerous sources. Suitable sources include bacteria, fungi and plants. EPSPS coding sequences from other sources can be obtained using the full-length petunia cDNA (see FIG. 4) or a suitable fragment thereof as a hybridization probe as described in Examples 1 and 14–17.

All peptide structures represented in the following description are shown in conventional format wherein the amino group at the N-terminus appears to the right. Likewise, amino acid nomenclature for the naturally occurring amino acids found in protein is as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V).

Those skilled in the art will recognize that mutant and variant forms of EPSPS may be made by a variety of processes. For example, cloning or expression vectors may be mutagenized to alter one or more amino acid residues in a EPSPS protein. This may be done on a random basis (e.g., by subjecting the host cells to mutagenic agents such as X-rays, ultraviolet light, or various chemicals), or by means involving an exact predicted substitution of bases in a DNA sequence. Alternately, one may select for a microbial source such as bacteria and fungi or a plant source having a mutant EPSPS exhibiting increased resistance to glyphosate.

A preferred EPSP synthase gene to be used is a variant form that encodes a glyphosate-tolerant EPSP synthase enzyme having a first sequence:

-L-G-N-A-A-T-A- located between positions 80 and 120 in the mature EPSP synthase amino acid sequence and having a second sequence:

$$E-R-P-I-x_1-x_2-L-V-x_3-x_4-L-x_5-x_6-x_7-\overset{D}{N}-A$$

where $x_1, x_2, x_3, x_4, x_6,$ and $x_7$ are any amino acid, and $x_5$ is either arginine or lysine, said second sequence located between positions 120 and 160 in the mature EPSP synthase amino acid sequence. In most cases the first sequence will be located between positions 90 and 110 and the second sequence will be located between 135 and 150 in the mature EPSP synthase. The gene further comprises a DNA sequence encoding a chloroplast transit peptide attached to the N-terminus of the mature EPSP synthase coding sequence, said transit peptide being adapted to facilitate the import of the EPSP synthase enzyme into the chloroplast of a plant cell.

While substituting either aspartic acid or asparagine for the glycine residue in the aforedescribed second conserved region results in a glyphosate resistant EPSP synthase, an aspartic acid substitution is most preferred. Those skilled in the art will recognize that substitutions of other amino acid residues are likely to yield EPSP synthase which are still glyphosate tolerant and possess a $K_m$ sufficient to maintain catalytic activity. Hence, other substitutions at this position should be considered within the spirit and scope of the present invention. Glyphosate-tolerant EPSP synthase genes are disclosed in our commonly assigned United States patent applications Ser. No. 07/179,245, filed on Apr. 22, 1988, now U.S. Pat. No. 4,971,908, and Ser. No. 07/380,963, filed on Jul. 17, 1989, the disclosures of which are hereby incorporated by reference.

The 3' non-translated region contains a polyadenylation signal which functions in plants to cause the addition of polyadenylate nucleotides to the 3' end of the EPSPS mRNA. In cases where the EPSPS sequence is derived from a plant source one can use the 3' non-translated region naturally associated with the particular EPSPS gene. Examples of other suitable 3' regions are the 3' transcribed, non-translated regions containing the polyadenylation signal of the nopaline synthase (NOS) gene of the Agrobacterium tumor-inducing (Ti) plasmid or the conglycinin (7S) storage protein gene.

The EPSPS gene of the present invention is inserted into the genome of a plant by any suitable method. Suitable plant transformation vectors include those derived from a Ti plasmid of *Agrobacterium tumefaciens* as well as those described in, e.g. Herrera-Estrella 1983, Bevan 1983, Klee 1985 and EPO publication 120,516 (Schilperoort et al.). In addition to plant transformation vectors derived from the Ti or root-inducing (Ri) plasmids of Agrobacterium, alternative methods can be used to insert the EPSPS genes of this invention into plant cells. Such methods may involve, for example, liposomes, electroporation, chemicals which increase free DNA uptake, and the use of viruses or pollen as vectors. If desired, more than one EPSPS gene may be inserted into the chromosomes of a plant, by methods such as repeating the trans-formation and selection cycle more than once.

EPSPS genes which encode an enzyme with a functional chloroplast transit peptide (which is preferably removed from the mature EPSPS polypeptide) also provide useful selectable marker genes for plant cell transformation, when transformed and untransformed cells are contacted with appropriate concentrations of glyphosate (which can be routinely determined for any type of plant). The conferrable trait of glyphosate resistance may be particularly useful with certain types of plants (such as alfalfa, soybean, and other legumes) which do not exhibit clear selectability using other selectable marker genes (such as kanamycin, methotrexate, or hygromycin resistance genes).

In addition, glyphosate-resistant plant cells that have been transformed with EPSPS genes can be regenerated into differentiated plants using standard nutrient media supplemented with selected shoot-inducing or root-inducing hormones, using methods described in PCT W084/02920 or other methods known to those skilled in the art.

As used herein, a EPSPS gene "confers a substantial degree of glyphosate resistance upon a plant cell" if it allows a selectable fraction of a culture of transformed plant cells to survive a concentration of glyphosate which kills essentially all untransformed cells from the same type of plant under the same conditions.

As used herein, a "cloning or expression vector" refers to a DNA or RNA molecule that is capable of replicating in one or more types of microbial cells. Vectors include plasmids, cosmids, viral DNA or RNA, minichromosomes, etc.

As used herein, "replicated from" includes indirect replication (e.g., replication of intermediate vectors), as well as replication directly from plant DNA or mRNA. It also includes DNA that is synthesized (e.g., by the method of Adams 1983) using a sequence of bases that is published or determined experimentally.

The following examples further demonstrate several preferred embodiments of this invention. Those skilled in the art will recognize numerous equivalents to the specific embodiments described herein. Such equivalents are intended to be within the scope of the claims.

EXAMPLES

Example 1: Creation of EPSPS Vectors

A. Creation of MP4-G Cell Line

The starting cell line, designated as the MP4 line, was derived from a Mitchell diploid petunia (see, e.g., Ausubel 1980). The MP4 cells were suspended in Murashige and Skoog (MS) culture media, (GIBCO, Grand Island, N.Y.) All transfer involved the transfer of 10 ml of suspension culture into 50 ml of fresh media. Cultivation periods until the next transfer ranged from 10 to 14 days, and were based on visual indications that the culture was approaching saturation.

Approximately 10 ml of saturated suspension culture (containing about $5\times10^6$ cells were transferred into 50 ml of MS media containing 0.5 mM glyphosate (Monsanto Agric. Products Co., St. Louis, Mo.). The sodium salt of glyphosate was used throughout the experiments described herein. The large majority of cells were unable to reproduce in the presence of the glyphosate. The cells which survived (estimated to be less than 1% of the starting population) were cultured in 0.5 mM glyphosate and transferred to fresh media containing glyphosate every 10 to 14 days.

After two transfers, the surviving cells were transferred into fresh media containing 1.0 mM glyphosate. After two transfers at 1.0 mM, the surviving cells were transferred sequentially into 2.5 mM glyphosate, 5.0 mM glyphosate, and 10 mM glyphosate. The MP4-G cells were subsequently shown (by a Southern blot) to have about 15-20 copies of the EPSPS gene, due to a genetic process called "gene amplification" (see, e.g., Schimke 1982). Although spontaneous mutations might have occurred during the replication of any cell, there is no indication that any mutation or other modification of the EPSPS gene occurred during the gene amplification process. The only known difference between the MP4 and the MP4-G cells is that the MP4-G cells contain multiple copies of an EPSPS gene and possibly other genes located near it on the chromosomes of the cells.

B. Purification and Sequencing of EPSPS Enzyme

Petunia cells from the MP4-G cell line were harvested by vacuum filtration, frozen under liquid $N_2$, and ground to a powder in a Waring blender. The powder was suspended into 0.2M tris-HCl, pH 7.8, containing 1 mM EDTA and 7.5% w/v polyvinyl-polypyrrolidone. The suspension was centrifuged at about 20,000 G for 10 min to remove cell debris. Nucleic acids were precipitated from the supernatant by addition of 0.1 volume of 1.4% protamine sulfate and discarded.

The crude protein suspension was purified by five sequential steps (see Mousdale 1984 and Steinrucken 1985) which involved: (1) ammonium sulfate precipitation; (2) diethylaminoethyl cellulose ion exchange chromatography; (3) hydroxyapatite chromatography; (4) sizing on a phenylagarose gel; and (5) sizing on a Sephacryl S-200 gel.

The purified EPSPS polypeptide was degraded into a series of individual amino acids by Edman degradation by a Model 470A Protein Sequencer (Applied Biosystems Inc., Foster City, Calif.), using the methods described in Hunkapiller 1983a. Each amino acid derivative was analyzed by reverse phase high performance liquid chromatography, as described by Hunkapiller 1983b, using a cyanopropyl column with over 22,000 theoretical plates (IBM Instruments, Wallingford, Conn.). A partial amino acid sequence for petunia EPSPS is shown in Table 1.

TABLE 1

| | PETUNIA EPSPS SEQUENCES | | | | | |
|---|---|---|---|---|---|---|
| | 8 | 9 | 10 | 11 | 12 | 13 |
| Amino acid: | Gln | Pro | Ile | Lys | Glu | Ile |
| mRNA strand: | 5'-CAP | CCN | AUU C A | GAP | CAP | AUU C A |
| Complementary DNA strand: | 3'-GTQ | GGN | TAA G | TTQ | CTQ | TAA G |

TABLE 1-continued

| PETUNIA EPSPS SEQUENCES | | | | | | |
|---|---|---|---|---|---|---|
| | 8 | 9 | 10 | 11 | 12 | 13 |
| | | | U | | | U |
| Synthetic DNA Probes: | | | | | | |
| EPSP1: | 3'-GTQ | GGP | TAP | TTQ | CTQ | TA |
| EPSP2: | 3'-GTQ | GGQ | TAP | TTQ | CTQ | TA |
| EPSP3: | 3'-GTQ | GGN | TAT | TTQ | CTQ | TA |
| Exact mRNA Sequence: | 5'-CAA | CCC | AUU | AAA | GAG | AUU |

C. Synthesis of Probes

Using the genetic code, the amino acid sequence indicated in Table 1 was used to determine the possible DNA codons which are capable of coding for each indicated amino acid. Using this information, three different probe mixtures were created and designated as EPSP-1, EPSP-2, and EPSP-3, as shown in Table 1. In this table, A, T, U, C, and G represent the nucleotide bases: adenine, thymine, uracil, cytosine and guanine. The letters P, Q, and N are variables; N represents any of the bases; P represents purines (A or G); Q represents pyrimidines (U, T, or C).

All oligonucleotides were synthesized by the method of Adams 1983. Whenever an indeterminate nucleotide position (P, Q, or N) was reached, a mixture of appropriate nucleotides was added to the reaction mixture. Probes were labeled 20 pmol at a time shortly before use with 100 uCi $\gamma$-[$^{32}$P]-ATP (Amersham) and 10 units of polynucleotide kinase in 50 mM Tris-HCl, pH 7.5, 10 mM MgCl$_2$, 5 mM DTT, 0.1 mM EDTA, and 0.1 mM spermidine. After incubation for 1 hr at 37° C., the probes were repurified on either a 20% acrylamide, 8M urea gel or by passage over a 5 ml column of Sephadex G25 in 0.1M NaCl, 10 mM Tris-HCl, pH 7.5, 1 mM EDTA.

D. Preparation of mRNA and Preliminary Testing of Probes (a) Poly-A mRNA

Total RNA was isolated from the MP4 (glyphosate sensitive) and MP4-G (glyphosate resistant) cell lines as described by Goldberg 1981. Total RNA was further sedimented through a CsCl cushion as described by Depicker 1982. Poly-A mRNA was selected by oligo-dT cellulose chromatography. The yield of poly-A RNA was 1.1 micrograms ($\mu$g) per gram of MP4 cells and 2.5 $\mu$g/gm of MP4-G cells.

(b) Gel Processing of RNA

Ten $\mu$g of poly-A RNA from the MP4 or MP4-G cell lines was precipitated with ethanol and resuspended in 1$\times$MOPS buffer (20 mM morpholino propane sulfonic acid, pH 7.0, 5 mM sodium acetate and 1 mM EDTA, pH 8.0) containing 50% formamide and 2.2M formaldehyde. RNA was denatured by heating at 65° C. for 10 min. One-fifth volume of a loading buffer containing 50% glycerol, 1 mM EDTA, 0.4% bromophenol blue and 0.4% xylene cyanol was then added. RNA was fractionated on a 1.3% agarose gel containing 1.1M formaldehyde until bromophenol blue was near the bottom. HaeIII-digested $\phi$X174 DNA, labelled with $^{32}$P, was run as a size standard. The DNA markers indicated approximate sizes for the RNA bands.

(c) Transfer of RNA to Nitrocellulose

RNA was transferred to nitrocellulose (#BA85, Schleicher & Schuell, Keene, N.H.) by blotting the gels overnight using 20$\times$SSC (1$\times$SSC is 0.15M NaCl, 0.015M sodium citrate, pH 7.0) as the transfer buffer. After transfer, filters were air-dried and baked in a vacuum oven for 2-3 hrs at 80° C.

(d) Preliminary Hybridization with Radioactive Probes

Filters were prehybridized in 6$\times$SSC, 10$\times$Denhardt's solution (1$\times$Denhardt's solution is 0.02% ficoll, 0.02% polyvinylpyrrolidone, 0.02% bovine serum albumin), 0.5% NP-40, and 200 $\mu$g/ml E. coli transfer RNA at 50° C. for 4 hrs. Hybridization was carried out in the fresh solution containing 2$\times$10$^6$ cpm/ml of either EPSP-1 or EPSP-2 probe for 48 hrs at 32° C. The EPSP-3 probe was not tested since it contained a codon (ATA) that is rarely used in the petunia genome. Hybridization temperature (32° C.) used in each case was 10° C. below the dissociation temperature (Td) calculated for the oligonucleotide with the lowest GC content in a mixture. The Td of the probe was approximated by the formula 2° C.$\times$(A+T)+4° C.$\times$(G+C).

(e) Filter Washing

The filters were washed twice for 15-20 min at room temperature in 6$\times$SSC and then for 5 min at 37° C. with gentle shaking. Filters were then wrapped in plastic film and autoradiographed for 12-14 hrs at −70° C. with two intensifying screens. The filters were then washed again for 5 min with gentle shaking at a temperature 5° C. higher than previously used. The filters were autoradiographed again for 12-14 hrs. The autoradiographs indicated that the probe EPSP-1 hybridized to an RNA of approximately 1.9 kb in the lane containing the poly-A RNA from the MP4-G cell line. No hybridization to this RNA was detected in the lane containing the poly-A RNA from the MP4 cell line. This result was attributed to overproduction of EPSPS mRNA by the MP4-G cell line. The probe EPSP-2, which differs from EPSP-1 by a single nucleotide, showed barely detectable hybridization to the 1.9 kb mRNA of the MP4-G cell line but hybridized strongly to a 1.0 kb mRNA from both cell lines. However, the 1.0 kb DNA was not sufficient to encode a polypeptide of 50,000 daltons, and it is believed that one of the sequences in the EPSP-2 probe hybridized to an entirely different sequence in the library. These results suggested that degenerate probe mixture EPSP-1 contained the correct sequence for EPSPS. This mixture was used in all subsequent degenerate probe hybridization experiments.

E. Preparation of $\lambda$gt 10 cDNA library (a) Materials Used

AMV reverse transcriptase was purchased from Seikagaku America, Inc., St. Petersburg, Fla.; the large fragment of DNA polymerase I (Klenow polymerase) was from New England Nuclear, Boston, Mass.; S1 nuclease and tRNA were from Sigma; AcA 34 column bed resin was from LKB, Gaithersburg, Md.; EcoRI, EcoRI methylase and EcoRI linkers were from New England Biolabs, Beverly Mass.; RNasin (ribonuclease inhibitor) was from Promega Biotech, Madison, Wis.

and all radioactive compounds were from Amersham, Arlington Hts., Ill.

The λgt10 vector (ATCC No. 40179) and associated *E. coli* cell lines were supplied by Thanh Huynh and Ronald Davis at Stanford University Medical School (see Huynh 1985). This vector has three important characteristics: (1) it has a unique EcoRI insertion site, which avoids the need to remove a center portion of DNA from the phage DNA before inserting new DNA; (2) DNA ranging in size from zero to about 8,000 bases can be cloned using this vector; and, (3) a library can be processed using *E. coli* MA150 cells (ATCC No. 53104) to remove clones which do not have DNA inserts.

(b) cDNA First Strand Synthesis

Poly-A mRNA was prepared as described in Example 1.D.a, and resuspended in 50 mM Tris (pH 8.5), 10 mM $MgCl_2$, 4 mM DTT, 40 mM KCl, 500 µM of d(AGCT)TP, 10 µg/ml $dT_{12-18}$ primer, and 27.5 units/ml RNasin. In a 120 µl reaction volume, 70 units reverse transcriptasen were added per 5 µg of poly-A RNA. One reaction tube contained $\phi$-$^{32}$P-dCTP (5 uCi/120 µl reaction) to allow monitoring of cDNA size and yield and to provide a first strand label to monitor later reactions. In order to disrupt mRNA secondary structure, mRNA in $H_2O$ was incubated at 70° C. for 3 min and the tube was chilled on ice. Reverse transcriptase was added and the cDNA synthesis was carried out at 42° C. for 60 min. The reaction was terminated by the addition of EDTA to 50 mM. cDNA yield was monitored by TCA precipitations of samples removed at the start of the reaction and after 60 min. Following cDNA synthesis, the cDNA existed as a cDNA-RNA hybrid. The cDNA-RNA hybrid was denatured by heating the mixture in a boiling water bath for 1.5 min, and cooled on ice.

(c) Second Strand DNA Synthesis

Single-stranded cDNA was allowed to self-prime for second strand synthesis. Both Klenow polymerase and reverse transcriptase were used to convert ss cDNA to ds cDNA. Klenow polymerase is employed first since its 3'-5' exonuclease repair function is believed to be able to digest non-flush DNA ends generated by self-priming and can then extend these flush ends with its polymerase activity. Reverse transcriptase is used in addition to Klenow polymerase, because reverse transcriptase is believed to be less likely to stop prematurely once it has bound to a template strand. The Klenow polymerase reaction was in a final 100 µl 1 volume excluding enzyme. The reaction mix included 50 mM HEPES, pH 6.9, 10 mM $MgCl_2$, 50 mM KCl, 500 µM of each dNTP and cDNA. To begin the reaction, 20 to 40 units of Klenow polymerase (usually less than 5 µl) were added and the tubes incubated at 15° C. for 5 hrs. The reaction was terminated by the addition of EDTA to 50 mM. The mix was extracted with phenol and the nucleic acids were precipitated, centrifuged and dried.

The reverse transcriptase reaction to further extend the anti-complementary DNA strand was performed as described for the reaction to originally synthesize cDNA, except $dT_{10-18}$ primer and RNasin were absent, and 32 units of reverse transcriptase, were used in a 120 µl reaction. The reaction was terminated by the addition of EDTA to 50 mM. The mixture was extracted with an equal volume of phenol and the nucleic acid was precipitated, centrifuged and dried.

(d) S1 Nuclease Treatment

200 µl of 2×S1 buffer (1×S1 buffer is 30 mM sodium acetate, pH 4.4, 250 mM NaCl, 1 mM $ZnCl_2$), 175 µl of $H_2O$ and 525 units of S1 nuclease were added to the tubes containing 125 µl of the second strand synthesis reaction product. The tubes were incubated at 37° C. for 30 min and the reaction was terminated by addition of EDTA to 50 mM. The mixture was extracted with an equal volume of phenol/chloroform (1:1). The aqueous phase was extracted with ether to remove residual phenol. The DNA was precipitated with ethanol and air dried.

(e) EcoRI Methylation Reaction

Since the ds cDNAs were copied from a large variety of mRNAs, many of the ds cDNAs probably contained internal EcoRI restriction sites. It was desired to protect such cleavage sites from EcoRI cleavage, to enable the use of blunt-ended EcoRI linkers which were subsequently cleaved with EcoRI to create cohesive overhangs at the termini.

In an effort to prevent the undesired cleavage of internal EcoRI sites, the ds cDNA was methylated using EcoRI methylase. DNA pellets were dissolved in 40 µl of 50 mM Tris pH 7.5, 1 mM EDTA, 5 mM DTT. Four µl of 100 µM S-adenosyl-L-methionine and 2 µl (80 units) of EcoRI methylase were added. Tubes were incubated at 37° C. for 15 min and then at 70° C. for 10 minutes to kill the methylase.

It was subsequently discovered that the methylation reaction described below was unsuccessful in preventing EcoRI cleavage at an internal site within the EPSPS coding region, apparently because of inactive methylase reagent. The cleavage of the internal EcoRI site required additional steps to isolate a full-length cDNA, as described below. To avoid those additional steps if another library is created, the methylation reagents and reaction conditions should be used simultaneously on the cDNA and on control fragments of DNA, and protection of the control fragments should be confirmed by EcoRI digestion before digestion is performed on the cDNA.

(f) DNA Polymerase I Fill-In Reaction

To the tube containing 45 µl of cDNA (prepared as described above) were added 5 µl of 0.1M $MgCl_2$, 5 µl of 0.2 mM d(ACGT)TP and 10 units of DNA polymerase I. The tube was incubated at room temperature for 10 min. The reaction was terminated by the addition of EDTA to 25 mM. One microgram of uncut λgt10 DNA was added as carrier and the mix was extracted with phenol/chloroform (1:1). The nucleic acid in the mix was precipitated with phenol/chloroform (1:1). The nucleic acid in the mix was precipitated with ethanol, centrifuged and dried.

(g) Ligation of EcoRI Linkers to Methylated ds cDNA

Approximately 400 pmoles of EcoRI linkers (5'CGGAATTCCG3') were dissolved in 9 µl of 20 mM Tris, pH 8.0, 10 mM MgCl, 10 mM DTT containing 50 µCi of α-$^{32}$P-ATP (5000 Ci/mmole) and 2 units of T4 polynucleotide kinase. The oligonucleotides were incubated at 37° C. for 30 minutes to allow them to anneal to each other, creating double-stranded, blunt-ended linkers. 2 units of T4 polynucleotide kinase and 1 µl of 10 mM ATP were added and incubated at 37° C. for an additional 30 min. The linkers were stored at −20° C. The methylated DNA pellet was resuspended in tubes containing 400 pmoles of the kinased linkers. Ligation of the EcoRI linkers to the methylated DNA was carried out by adding 1 µl of T4 ligase and incubating the reaction mixture at 12°-14° C. for 2 days.

(h) Digestion with EcoRI to Create Cohesive Termini

To 11 μl of the reaction product from Example 1.E.(g), 10 μl of a solution containing 50 mM Tris, pH 7.5, 10 mM MgSO4, 200 mM NaCl were added. T4 DNA ligase was heat inactivated by incubation at 70° C. for 10 min. Forty units of EcoRI were added an the incubation was carried out at 37° C. for 3 hr. The reaction was terminated by addition of EDTA to 50 mM. The sample was clarified by centrifugation and applied to an AcA 34 column.

(i) AcA 34 Column Chromatography

Free linkers (those not ligated to ds cDNA) were removed from ds cDNA with attached linkers, to prevent them from interfering with the insertion of the desired ds cDNAs into the cloning vectors. AcA 34 resin (a mixture of acrylamide and agarose beads, normally used for sizing) preswollen in 2 mM citrate buffer and 0.04% sodium azide in water, was added to the 1 ml mark of a 1 ml plastic syringe plugged with glass wool. The column was equilibrated with 10 mM Tris-HCl pH 7.5, 1 mM EDTA, 400 mM NaCl. The ds cDNA mixtures with ligated linkers and free linkers (~45 μl) was brought to 400 mM NaCl. 1 μl of 0.5% bromophenol blue dye (BPB) was added, and the sample was applied to the column which was run in equilibration buffer at room temperature. Ten 200 μl fractions were collected. The BPB dye normally eluted from the column in the sixth tube or later. Tubes 1 and 2 were combined and used as the source of ds cDNA for cloning.

(j) Assembly of λgt10 clones

The ds cDNA was mixed with 1 μg of EcoRI-cut λgt10 DNA, precipitated with ethanol, and centrifuged. After washing the pellet once with 70% ethanol, the DNA pellet was air dried and resuspended in 4.5 μl of 10 mM Tris-HCl pH 7.5, 10 mM MgCl2, 50 mM NaCl. To anneal and ligate the cDNA inserts to the left and right arms of the λgt10 DNA, the mixture was heated at 70° C. for 3 min., then at 50° C. for 15 min. The mixture was chilled on ice, and 0.5 μl each of 10 mM ATP, 0.1M DTT, and sufficient T4 DNA ligase to ensure at least 90% completion were added. The reaction was incubated at 14° C. overnight, which allowed the insertion of the ds cDNA into the EcoRI site of the λgt10 DNA. The resulting DNA was packaged into phage particles in vitro using the method described by Scherer 1981.

(k) Removal of Phages Without Inserts

Insertion of a cDNA into the EcoRI site of λgt10 results in inactivation of the C1 gene. λgt10 phages with inactivated C1 genes (i.e., with inserts) replicate normally in E. coli MA150 cells. By contrast, λgt10 phages without inserts are unable to replicate in the MA150 strain of E. coli. This provides a method of removing λgt10 clones which do not have inserts.

The phages in the library were first replicated in E. coli C600 (M+R−) cells which modified the λgt10 DNA to protect it from the E. coli MA150 restriction system. A relatively small number of E. coli C600 cells were infected and then plated with a 20 fold excess of MA150 (M+R−) cells. The primary infection thus occurred in the M+R− cells where all the phages will grow, but successive rounds of replication occurred in the MA150 cells which prevented the replication of phages without inserts. The amplified phage library was collected from the plates, and after removal of agar and other contaminants by centrifugation, the recombinant phages were ready to use in screening experiments.

F. Screening of cDNA Library; Selection of pMON9531

Approximately 6000 phages (each plate) were spread on 10 cm×10 cm square plates of solid NZY agar (Maniatis 1982) with 0.7% agarose. A translucent lawn of E. coli MA150 cells was growing on the plates. Areas where the phages infected and killed the E. coli cells were indicated by clear areas called "plaques", which were visible against the lawn of bacteria after an overnight incubation of the plates at 37° C. Six plates were prepared in this manner. The plaques were pressed against pre-cut nitrocellulose filters for about 30 min. This formed a symmetrical replica of the plaques. To affix the phage DNA, the filters were treated with 0.5M NaOH and 2.5M NaCl for 5 min. The filters were then treated sequentially with 1.0M Tris-HCl, pH 7.5 and 0.5M Tris-HCl, pH 7.5 containing 2.5M NaCl to neutralize the NaOH. They were then soaked in chloroform to remove bacterial debris. They were then air-dried and baked under a vacuum at 80° C. for 2 hr, and allowed to cool to room temperature. The filters were then hybridized with $^{32}$P-labelled EPSP-1 probe ($2 \times 10^6$ cpm/filter) as described in Example 1.D(e). After 48 hr of hybridization, the filters were washed in 6×SSC at room temperature twice for 20 min and then at 37° C. for 5 min. These washes removed non-specifically bound probe molecules, while probe molecules with the exact corresponding sequence (which was unknown at the time) remained bound to the phage DNA on the filter. The filters were analyzed by autoradiography after the final wash. After the first screening step, seven positively hybridizing signals appeared as black spots on the autoradiograms. These plaques were removed from the plates and replated on the fresh plates at a density of 100-200 plaques/plate. These plates were screened using the procedure described above. Four positively hybridizing phages were selected. DNA was isolated from each of these four clones and digested with EcoRI to determine the sizes of the cDNA inserts. The clone containing the largest cDNA insert, approximately 330 bp, was selected, and designated λE3. The cDNA insert from λE3 was inserted into plasmid pUC9 (Vieira 1981), and the resulting plasmid was designated pMON9531.

To provide confirmation that the pMON9531 clone contained the desired EPSPS sequence, the insert was removed from the pMON9531 clone by digestion with EcoRI. This DNA fragment was then sequenced by the chemical degradation method of Maxam 1977. The amino acid sequence deduced from the nucleotide sequence corresponded to the EPSPS partial amino acid sequence shown in Table 1.

G. Creation of λF7 Genomic DNA Clone

In order to obtain the entire EPSPS gene, chromosomal DNA from the MP4-G cells line was digested with BamHI and cloned into a phage vector to create a library, which was screened using the partial EPSPS sequence from pMON9531 as a probe.

(a) Preparation of MP4-G Chromosomal DNA Fragments

MG4-G cells were frozen and pulverized in a mortar with crushed glass in the presence of liquid nitrogen. The powdered cells were mixed with 8 ml/g of cold lysis buffer containing 8.0M urea, 0.35M NaCl, 0.05M Tris-HCL(pH 7.5), 0.02M EDTA, 2% sarkosyl and 5% phenol. The mixture was stirred with a glass rod to break up large clumps. An equal volume of a 3.1 mixture of phenol and chloroform containing 5% isoamyl alcohol was added. Sodium dodecyl sulfate (SDS) was added to a final concentration of 0.5%. The mixture was swirled on a rotating platform for 10-15 minutes at room temperature. The phases were separated by centrifugation at 6,000×g for 15 minutes. The phenol/chloroform extraction was repeated. Sodium acetate was added to the aqueous phase to a final concentration of 0.15M and the DNA was precipitated with ethanol. The DNA was collected by centrifugation, dissolved in 1×TE (10mM Tris-HCl, pH 8.0, 1 mM EDTA) and banded in a CsCl-ethidium bromide gradient. The DNA was collected by puncturing the side of the tube with a 16 gauge needle. The ethidium bromide was extracted with CsCl-saturated isopropanol, and the DNA was dialyzed extensively against 1×TE. Approximately 400 μg of DNA was isolated from 12 g of cells.

MP4-G chromosomal DNA (10 μg) was digested to completion with 30 units of BamHI in a buffer containing 10 mM Tris, pH 7.8, 1 mM DTT, 10mM $MgCl_2$, 50 mM NaCl for 2 hours at 37° C. The DNA was extracted with phenol followed by extraction with chloroform and precipitated with ethanol. The DNA fragments were suspended in 1×TE at a concentration of 0.5 μg/μl.

(b) Cloning of MP4-G Chromosomal DNA Fragments in μMG14

DNA from phage μMG14 (obtained from Dr. Maynard Olson of the Washington University School of Medicine, St. Louis, Mo.) was prepared by the method described in Maniatis 1982. 150 μg of DNA was digested to completion with BamHI in a buffer containing 10mM Tris-HCl, pH 7.8, 1 mM DTT, 10 mM $MgCl_2$, 50 mM NaCl. The completion of the digest was checked by electrophoresis through 0.5% agarose gel. The phage DNA was then extracted twice with phenol-chloroform-isoamyl alcohol (25:24:1) and precipitated with ethanol. The DNA was resuspended in 1×TE at a concentration of 150 μg/ml. $MgCl_2$ was added to 10 mM and incubated at 42° C. for 1 hr to allow the cohesive ends of λDNA to reanneal. Annealing was checked by agarose gel electrophoresis.

After annealing, DNA was layered over a 38 ml (10-40%, w/v) sucrose gradient in a Beckman SW27 ultracentrifuge tube. The gradient solutions were prepared in a buffer containing 1M NaCl, 20 mM Tris-HCl (pH 8.0), 5 mM EDTA. 75 μg of DNA was loaded onto each gradient. The samples were centrifuged at 26,000 rpm for 24 hours at 15° C. in a Beckman SW 27 rotor. Fractions (0.5 ml) were collected from the top of the centrifuge tube and analyzed for the presence of DNA by gel electrophoresis. The fractions containing the annealed left and right arms of λDNA were pooled together, dialyzed against TE and ethanol-precipitated. The precipitate was washed with 70% ethanol and dried. The DNA was dissolved in TE at a concentration of 500 μg/ml.

The purified arms of the vector DNA and the BamHI fragments of MP4-G DNA were mixed at a molar ratio of 4:1 and 2:1 and ligated using TfDNA ligase in a ligase buffer containing 66 mM Tris-HCl, pH 7.5, 5 mM MgCl, 5 mM DTT and 1 mM ATP. Ligations was carried out overnight at 15° C. Ligation was checked by agarose gel eletrophoresis. Ligated phase DNA carrying inserts of MP4-GDNA were packaged into phage capsids in vitro using commercially available packaging extracts (Promega Biotech, Madison, Wis.). The packaged phage were plated on 10 cm×10 cm square plates of NZY agar in 0.7% agarose at a density of approximately 6000 plaques per plate using E. coli C600 cells. After overnight incubation at 37° C., the plaques had formed, and the plates were removed from the incubator and chilled at 4° C. for at least an hour. The agar plates were pressed against nitrocellulose filters for 30 minutes to transfer phages to the filters, and the phage DNA was affixed to the filters as described previously. Each filter was hybridized for 40 hours at 42° C. with approximately $1.0 \times 10^6$ cpm/filter of the 330 bp cDNA insert isolated from the pMON9531 clone, which had been nick-translated, using the procedure described in Maniatis 1982. The specific activity of the probe was $2-3 \times 10^8$ cpm/μg of DNA. Hybridization was carried out in a solution containing 50% formamide, 5×SSC, 5×Denhardt's solution, 200 μg/ml tRNA and 0.1% SDS. Filters were washed in 1×SSC, 0.2% SDS at 50° C. and autoradiographed. Several positive signals were observed, and matched with plaques on the corresponding plate. The selected plaques were lifted, suspended in SM buffer, and plated on NYZ agar. The replica plate screening process was repeated at lower densities until all the plaques on the plates showed positive signals. One isolate was selected for further analysis and was designated as the λF7 phage clone.

H. Creation of pMON9543 and pMON9556

The DNA from λF7 was digested (separately) with BamHI, BglII, EcoRI, and HindIII. The DNA was hybridized with a nick translated EPSPS sequence from pMON9531 in a Southern blot procedure. This indicated that the complementary sequence from λF7 was on a 4.8 kb BglII fragment. This fragment was inserted into plasmid pUC9 (Vieira 1982), replicated, nick translated, and used to probe the petunia cDNA library, using hybridization conditions as described in Example 1.G, using $10^6$ cpm per filter. A cDNA clone with a sequence that bound to the λF7 sequence was identified, and designated as pMON9543.

DNA sequence analysis (Maxam 1977) indicated that pMON9543 did not contain the stop codon or the 3' non-translated region of the EPSPS gene. Therefore, the EPSPS sequence was removed from pMON9543, nick translated, and used as a probe to screen the cDNA library again. A clone which hybridized with the EPSPS sequence was identified and designated as pMON9556. DNA sequence analysis indicated that the insert in this clone contained the entire 3' region of the EPSPS gene, including a polyadenylated tail. The 5' EcoRI end of this insert matched the 3' EcoRI end of the EPSPS insert in pMON9531. An entire EPSPS coding sequence was created by ligating the EPSPS inserts from pMON9531 and pMON9556.

I. Creation of pMON546 Vector with CaMV 35S/EPSPS Gene

Figure 2:
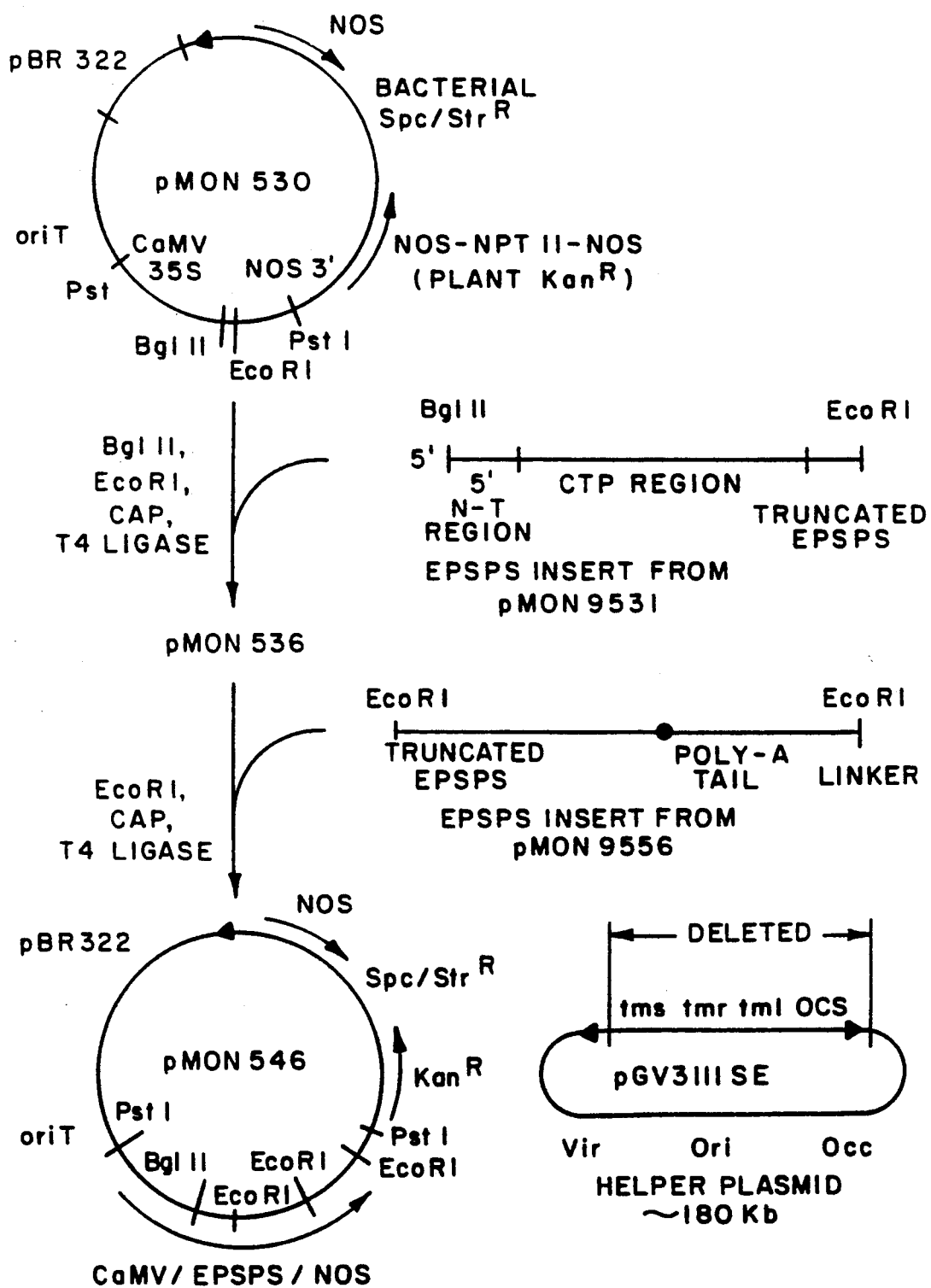
FIG. 2 depicts the creation of plasmid pMON546, a plant transformation vector which contains a chimeric CaMV/EPSPS gene. It also depicts the structure of pGV3111-SE, a disarmed Ti plasmid with vir genes which help insert the CaMV/EPSPS gene from pMON546 into plant chromosomes.
Figure 5:
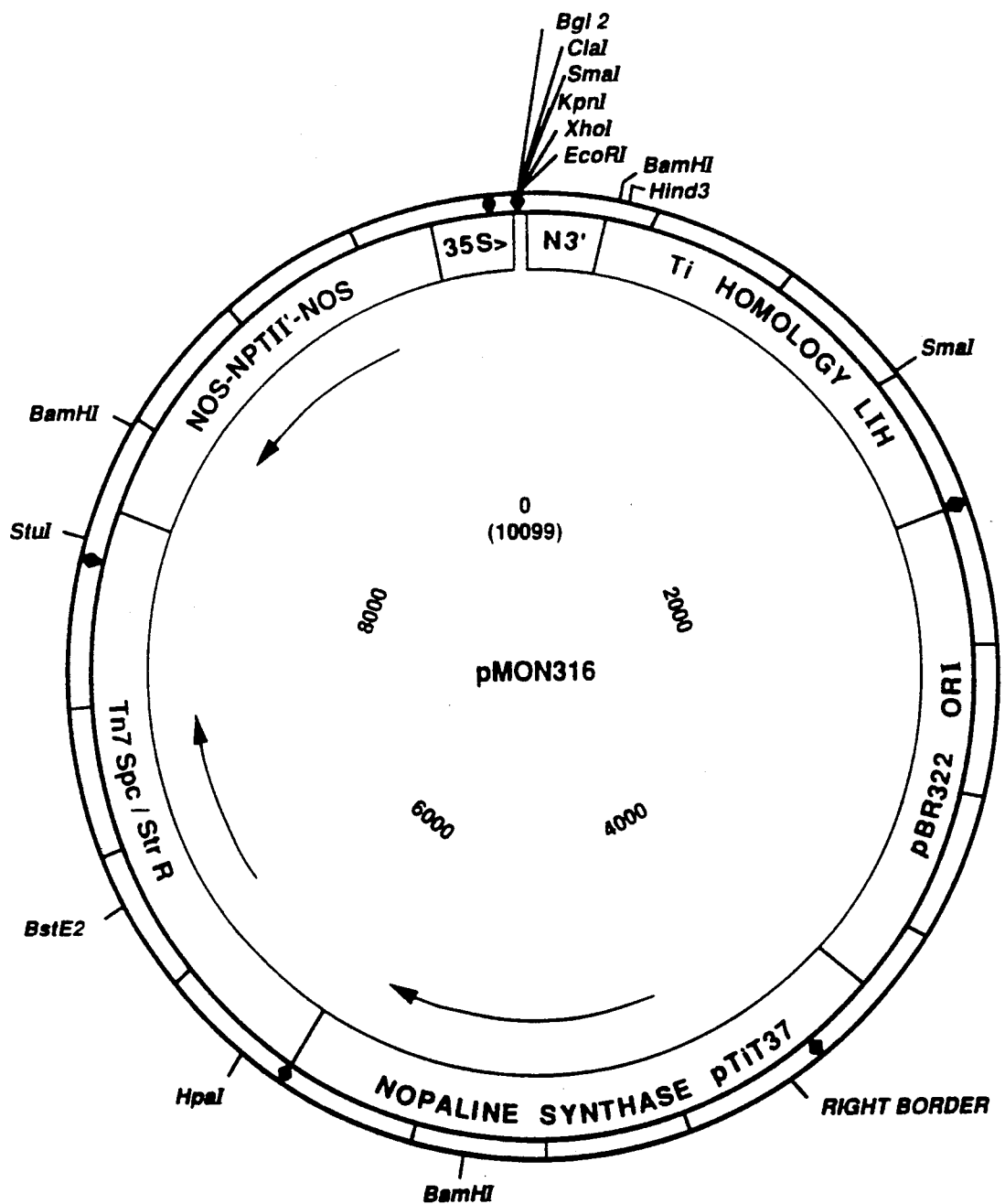
FIG. 5 shows the plasmid map for pMON316.

The EPSPS insert in pMON9531 was modified by site-directed mutagenesis (Zoller et al, 1983) using an M13 vector (Messing 1981 and 1982) to create a BglII site in the 5' non-translated region of the EPSPS gene. The modified EPSPS sequence was isolated by EcoRI and BglII digestion, and inserted into a plant transformation vector, pMON530, to obtain pMON536, as shown in FIG. 2. pMON530, a derivative of pMON505 carrying the 35S-NOS cassette, was created by transferring the 2.3 kb StuI-HindIII fragment of pMON316 into pMON526. Plasmid pMON316 (see FIG. 5) is a co-integrating type intermediate vector with unique cleavage sites for the restriction endonucleases BglII, ClaI, KpnI, XhoI and EcoRI located between the 5' leader and the NOS polyadenylation signals. The cleavage sites provide for the insertion of coding sequences carrying their own translational initiation signals immediately adjacent to the CaMV 35S transcript leader sequence. The 316 plasmid retains all of the properties of pMON200 including spectinomycin resistance for selection in *E. coli* and *A. tumefaciens* as well as a chimeric kanamycin gene (NOS/NPTII/NOS) for selection of transformed plant tissue and the nopaline synthase gene for ready scoring of transformants and inheritance in progeny. Plasmid pMON526 is a simple derivative of pMON505 in which the SmaI site was removed by digestion with XmaI, treatment with Klenow polymerase and ligation. The resultant plasmid, pMON530 (FIG. 2) retains the properties of pMON505 and the 35S-NOS expression cassette now contains a unique cleavage site for SmaI between the promoter and poly-adenylation signals. The 1.62 kb EcoRI-EcoRI fragment from pMON9556 was then inserted into pMON536 to obtain pMON546. Since pMON530 already contained a 35S promoter from a cauliflower mosaic virus (CaMV) next to the BglII site, this created a chimeric CaMV/EPSPS gene in pMON546.

As shown in FIG. 2, plasmid pMON546 contained (1) the CaMV 35S/EPSPS gene; (2) a selectable marker gene for kanamycin resistance (KanR); (3) a nopaline synthase (NOS) gene as a scorable marker; and (4) a right T-DNA border, which effectively caused the entire plasmid to be treated as a "transfer DNA" (T-DNA) region by *A. tumefaciens* cells. This plasmid was inserted into *A. tumefaciens* cells which contained a helper plasmid, pGV3111SE. The helper plasmid encodes certain enzymes which are necessary to cause DNA from pMON546 to be inserted into plant cell chromosomes. It also contains a kanamycin resistance gene which functions in bacteria.

A culture of *A. tumefaciens* containing pMON546 and pGV3111-SE was deposited with the American Type Culture Collection (ATCC) and was assigned ATCC accession number 53213. If desired, either one of these plasmids may be isolated from this culture of cells using standard methodology. For example, these cells may be cultured with *E. coli* cells which contain a mobilization plasmid, such as pRK2013 (Ditta 1980). Cells which become Spc/strR, kanS will contain pMON546, while cells which become KanR, spc/strS will contain pGV3111-SE.

Example 2: GLY$^R$ Petunia Cells

Leaf disks with diameters of 6 mm (¼ inch) were taken from surface-sterilized petunia leaves. They were cultivated on MS104 agar medium for 2 days to promote partial cell wall formation at the wound surfaces. They were then submerged in a culture of *A. tumefaciens* cells containing both pMON546 and GV3111-SE which had been grown overnight in Luria broth at 28° C., and shaken gently. The cells were removed from the bacterial suspension, blotted dry, and incubated upside down on filter paper placed over "nurse" cultures of tobacco cells, as described in Horsch 1981. Afer 2 or 3 days, the disks were transferred to petri dishes containing MS media with 500 μg/ml carbenicillin and 0, 0.1, 0.25, or 0.5 mM glyphosate (sodium salt), with no nurse cultures.

Control tissue was created using *A. tumefaciens* cells containing the helper plasmid pGV3111-SE and a different plant transformation vector, pMON505, which contained a T-DNA region with a NOS/NPTII/NOS kanamycin resistance gene and a NOS selectable marker gene identical to pMON546, but without the CaMV/EPSPS gene.

Within 10 days after transfer to the media containing glyphosate, actively growing callus tissue appeared on the periphery of all disks on the control plate containing no glyphosate. On media containing 0.1 mM glyphosate, there was little detectable difference between the control disks and the transformed tissue. At 0.25 mM glyphosate, there was very little growth of callus from control disks, while substantial growth of transformed tissue occurred. At 0.5 mM glyphosate, there was no callus growth from the control disks, while a significant number of calli grew from the transformed disks. This confirms that the CaMV/EPSPS gene conferred glyphosate resistance upon the transformed cells.

Example 3: GLY$^R$ Tobacco Cells

Leaf disks were excised from tobacco plants (*N. tabacum*) and treated as described above with *A. tumefaciens* cells containing pMON546 (or pMON505, for control cells) and helper plasmid pGV3111-SE. The cells transformed with the CaMV/EPSPS gene created substantial amounts of callus tissue on 0.5 mM glyphosate, whereas the cells which did not contain that gene did not create any detectable callus tissue.

Example 4: GLY$^R$ Soybean Cells

Sterile hypocotyl pieces of *Glycine canescens*, a type of soybean, were infected with the *A. tumefaciens* strain containing the chimeric EPSPS gene as described in Example 2. Nurse culture plates were made which contained a medium of 10% of the normal level of MS salts (GIBCO), B5 vitamins, 3 g/l sucrose, 2 mg/l napthalene acetic acid, 1 mg/l benzyladenine, and 0.5 mM arginine. The pH was adjusted to 5.7 before autoclaving.

The infected soybean hypocotyls were incubated at 26° C. for two days and transferred to a similar medium (except that the MS salts were not diluted) and additionally containing 500 mg/l carbenicillin, 100 mg/l cefotaxime and 100 mg/l kanamycin. Under these conditions, only transformed soybean callus was able to grow.

Control tissue was produced using *A. tumefaciens* cells containing the helper Ti plasmid pTiT37-SE and a plant transformation vector pMON200. See Fraley et al, Biotechnology Vol. 3, 1985, described herein. The co-integrate pTiT37-SE contained a T-DNA region with a NOS/NPTII/NOS kanamycin resistance gene and a NOS scorable marker gene identical to pMON200, but without the CaMV 35S/EPSPS/NOS gene.

This disarmed nopaline-type Ti plasmid was created from pTiT37 in a manner analogous to that described by Fraley et al. (1985) for creating the pTiB6S3-SE disarmed octopine-type Ti plasmid. The general procedure is to replace most of the pTiT37 T-DNA with a selectable marker and pBR322 and LIH segments from pMON200 to provide a region of homology for recombination with pMON200 and derivatives. This replacement results in the deletion of the rightmost approximately 80 percent of the T-DNA including the phytohormone biosynthetic genes, nopaline synthase gene and the right border of the T-DNA.

The source of the pTiT37 sequences was the plasmid MINI-Ti described by deFramond et al. (Bio/Technology 1: 262, 1983). This plasmid is a convenient source; however, these same Ti plasmid segments could be obtained directly from the pTiT37 or related pTiC58 plasmid or from subclones of these plasmids isolated by others such as those described by Hepburn et al. (J. Mol. Appl. Genetics 2: 211–224, 1983) or Zahm et al. (Mol Gen Genet 194: 188–194, 1984).

Plasmid MINI-Ti is a derivative of pBR325 carrying the pTiT37 KpnI fragments 13b, 4 and 11 (deFramond et al., 1983) which are analogous to the pTiC58 KpnI fragments 13, 3 and 12 (Depicker et al., Plasmid 3: 193–211, 1980). The internal T-DNA sequences including the phytohormone biosynthetic genes and right border were removed from mini-Ti by digestion with HindIII and religation to produce pMON284. The pMON284 plasmid contains a unique KpnI site which was converted to a BamHI site by cleavage with KpnI and insertion of the following synthetic linker:

```
5'-   CGGATCCGGTAC
      CATGGCCTAGGC
``` which contains a BamHI site (5'-GGATCC) in the the center of the linker. A plasmid that contains this linker was isolated and called pMON293.

The pMON293 plasmid carries the following pTiT37 fragments adjacent to each other in inverted orientation with respect to their orientation in the Ti plasmid and joined through a BamHI linker. First is the KpnI site at the right end of the 13b fragment. This fragment contains the left border of the pTiT37 T-DNA. Then comes the left end of the 13b fragment joined to the BamHI linker. Joined to this is the right end of the KpnI 11 fragment. This fragment contains Ti plasmid located to the right of the T-DNA and ends with a HindIII site that is the right end of the pTiC58 HindIII 2 fragment (Depicker et al., 1980). This is joined to the pBR325 derivative plasmid which also is fused to the KpnI site at the right end of the KpnI 13b fragment.

To introduce homology to pMON200 and a kanamycin resistance selectable marker for *A. tumefaciens* between the pTiT37 segments, we constructed plasmid pMON292. Plasmid pMON292 is a derivative of pMON113 which consists of the 2.6 kb pBR322 PvuII to HindIII fragment joined to the 1.7 kb BglII (nucleotide 1617) to HindIII (nucleotide 3390, Barker et al., Plant Mol. Biology 2: 335, 1983) fragment of octopine type T-DNA of pTiA6. This segment, called the LIH, has been previously described by Fraley et al. (1985). The BglII site was made flush ended by treatment with Klenow polymerase before ligation with the pBR322 segment.

Plasmid pMON113 was cleaved with HindIII, treated with Klenow polymerase and joined to the 1.2 kb AvaII fragment of Tn903 Oka et al. *J. Mol. Biol.* 147:217 (1981) (601) that had been treated with Klenow polymerase, ligated to synthetic BamHI linkers, digested with BamHI and treated again with Klenow polymerase. The resulting plasmid carrying the Tn903 kanamycin resistance determinant adjacent to the LIH segment was called pMON292.

The pMON200 homology region and bacterial kanamycin resistance marker were inserted between the pTiT37 segments by mixing pMON292 linearized by cleavage with HincII with two fragments derived from pMON293: a 2.5 kb PvuII-BamHI fragment and a 4.5 kb fragment isolated after cleavage with HindIII, Klenow polymerase treatment, and cleavage with BamHI. The resulting plasmid, pMON313, carries the following fragments in this order. First, is the BamHI linker followed by a 4.5 kb KpnI-HindIII fragment derived from the right side of pTiT37 KpnI fragment 11. This is joined to the 750 bp HincII-HindIII segment of pBR322 followed by the 1.2 kb Tn903 segment encoding kanamycin resistance. This is followed by the LIH (HindIII-BglII segment and the PvuII-HincII segment of pBR322 that carries the origin of replication. Next, there is a 2.5 kb PvuII to KpnI fragment from the left end of the pTiT37 KpnI 13b fragment which contains the left border of the T-DNA. Finally, this is joined to the starting BamHI linker.

To introduce this DNA into Agrobacterium, pMON313 was cleaved with BamHI and mixed with pRK290 DNA that had been cleaved with BglII and treated with DNA ligase. A derivative of pRK290 carrying the pMON313 plasmid was isolated and called pMON318.

Plasmid pMON318 was introduced into *Agrobacterium tumefaciens* strain A208 which carries pTiT37 and a chromosomal chloramphenicol resistance by standard bacterial mating methods using pRK2013 as a helper. This method and subsequent selection for the replacement of the T-DNA with the engineered T-DNA segment carried in pMON318 was exactly as described by Fraley et al. (1985) for the selection of the disarmed octopine-type pTiB6S3-SE plasmid.

The resultant disarmed pTiT37-SE plasmid contains the vir region intact and retains the left T-DNA border and approximately 1 kb of the T-DNA. This region of the T-DNA has not been reported to encode a transcript (Joos et al., Cell 32: 1057–1067, 1983. This is followed by the pBR322 segment and LIH and then the Tn903 kanamycin resistance. The Tn903 segment is joined to a 750 bp segment of pBR322 that is joined to the left end of the pTiT37 analogue of the pTiC58 HindIII 2 fragment (Depicker et al., 1980). This fragment is located outside the right end of the pTiT37 T-DNA. The result is that over 90% of the T-DNA including the phytohormone biosynthetic genes responsible for crown gall disease production and right border are absent from the pTiT37-SE plasmid.

The pTiT37-SE plasmid is carried in a derivative of strain A208 that was selected for growth in 25 µg/ml chloramphenicol and this strain with the disarmed plasmid is called A208-SE or ASE. The A208-SE strain is used as a recipient for the pMON200 intermediate vector in the triple mating procedure in exactly the same manner as the 3111-SE strain (Fraley et al., 1985). This results in a co-integrate hybrid T-DNA consisting of the following from left to right: the pTiT37 left border and approximately 1 kb of sequence just inside the border, the pBR322 HincII to PvuII segment, the pTiA6 BglII to HindIII LIH region, the pMON200 synthetic multilinker, the NOS/NPTII/NOS kanamycin resistance gene for selection in plants, the Tn7 spectinomycin/streptomycin resistance determinant, the nopaline synthase gene as a scorable marker for plant cells, the right border of the pTiT37 T-DNA. The DNA between the two border sequences just described and any other DNA inserted into the analogous region of pMON200 and derivatives are transferred to plant cells during the trans-formation procedure.

After 14-17 days, soybean callus transformed with either the vector alone (pMON200 plasmid) or with the vector containing a chimeric EPSPS gene was transferred to petri dishes containing MS medium and 0, 0.5 mM or 1.0 mM glyphosate.

Within 18-20 days after transfer to the media containing glyphosate, actively growing callus tissue appeared in all dishes containing no glyphosate.

On medium containing 0.5 mM glyphosate there was little growth in the dishes containing control callus, i.e., the callus contain the pMON200 vector alone, while some callus colonies containing the chimeric EPSPS gene described hereinbefore in FIG. 2 showed definite growth. At 1.0 mM glyphosate, there was no callus growth from the control tissues and again, some growth of the transformed callus containing the chimeric EPSPS gene. This confirms that the CaMV 35S/EPSPS/NOS gene conferred glyphosate resistance on the soybean cells.

Example 5: Gly$^R$ Cotton Cells

A plant transformation vector similar to pMON546 is prepared following the general procedure outlined in Example 1 except that the CTP/EPSPS coding sequence is obtained from cotton. Seeds of cotton (cultivator Delta Pine 50) are surface sterilized using sodium hypochlorite and germinated in vitro on a basal medium in the dark. After 2 weeks hypocotyls and cotyledons are cut into pieces and innoculated with a tumorous strain of *A. tumefaciens* containing the above described transformation vector and helper plasmid pGV3111. After 3 days coculture on MS basal medium, the explants are transferred to the same medium with 500 mg/l carbenicillin to kill the bacteria. After 2 to 4 weeks, tumor tissue is transferred to the same medium containing 0.5 mM glyphosate.

Control tissue was produced using tumorous *A. tumefaciens* cells containing the helper plasmid pGV3111 and pMON200. Tissue transformed with the above-described transformation vector demonstrates glyphosate resistance by continuing growth while growth of pMON200 transformed tissue (control) and non-transformed tissue is inhibited.

Example 6: Gly$^R$ Oil Seed Rape Cells

A plant transformation vector similar to pMON546 is prepared following the procedure outlined in Example 1 except that the CTP/EPSPS coding sequence is obtained from rape plant such as *Brassica napus* (see Example 17). Alternately, a genomic clone of the EPSP synthase from *Brassica napus* or *Arabidopsis thaliana* can be used as described in Example 20.

The four terminal intervals from *B. napus* plants (growth chamber grown in soil) are surface sterilized in sodium hypochlorite and cut into 5 mm sections. The upper surface of each piece is inoculated with an overnight liquid culture of *A. tumefaciens* containing the above described transformation vector and helper plasmid pTiT37-SE and incubated for 2 to 3 days on nurse culture plates containing 1/10 MS medium with 1 mg/l BA. The explants are then transferred to MS medium containing 1 mg/l BA, 500 mg/l carbenicillin and 100 mg/l kanamycin. After 3 to 6 weeks, leaf tissue from transgenic shoots that have developed is transferred to the same medium but with 0.5 mM glyphosate instead of the kanamycin to test for tolerance.

Control tissue is prepared using *A. tumefaciens* cells containing helper plasmid pTiT37-SE and vector pMON200. Transgenic tissue that expresses EPSPS are able to grow in the presence of glyphosate while transformed and non-transformed controls are inhibited.

Example 7: Gly$^R$ Flax Cells

A plant transformation vector similar to pMON546 is prepared following the procedure outlined in Examples 1, and 14-17 except that the CTP/EPSPS coding sequence is obtained from flax.

Flax seeds are surface-sterilized with 70% ethanol, 25% Chlorox and rinsed with sterile distilled water. The seeds are placed on solid MS medium and allowed to germinate in the light for 5-7 days. The hypocotyls are removed aseptically and inoculated with *A. tumefaciens* cells containing the above-described transformation vector and helper plasmid pTiB6S3-SE or pTiT37-SE and permitted to co-culture for 2 days on MS medium containing 1 mg/l benzylaminopurine, 0.02 mg/l naphthalene acetic acid and 4% sucrose. The hypocotyls are then placed on MS medium supplemented with 400 mg/l kanamycin and 500 mg/l carbenicillin. After 2 weeks, selection for transformed callus and shoots are evident. The original explant begins to turn brown and the non-transformed initially formed shoots bleach white. The selected callus and shoots are green and opine positive.

Control tissue is prepared using *A. tumefaciens* cells containing helper plasmid pTiB6S3-SE or pTiT37-SE and vector pMON200. Selected callus transformed with the above-described EPSPS vector demonstrates resistance to glyphosate at concentrations between 5.0 and 20.0 mM. Control tissue bleaches and dies at these glyphosate levels.

Example 8: Isolation of Mutant EPSPS Gene from *E. coli*

Cells of *E. coli* ATCC 11303 were transferred to medium A and incubated at 37° C.

| MEDIUM A | |
|---|---|
| 10 X MOPS medium | 50 ml |
| 50% glucose solution | 2 ml |
| 100 mM aminomethyl phosphonate | 2 ml |
| Thiamine (5 mg/ml), pH 7.4 | 1 ml |
| 100 mM Glyphosate (sodium salt) | 2 ml |
| Deionized water to | 500 ml |
| 10 X MOPS medium: | Per 500 ml |
| 1 M MOPS (209.3 g/l, pH 7.4 | 200 ml |
| 1 M Tricine/89.6 g/l, pH 7.4) | 20 ml |
| 0.01 M FeSO$_4$, 7H$_2$O (278.01 mg/100 ml) | 5 ml |
| 1.9 M NH$_4$Cl (50.18 g/500 ml) | 25 ml |
| .276 M K$_2$SO$_4$ (4.81 g/100 ml) | 5 ml |
| 0.5 mM CaCl$_2$, 2H$_2$O (7.35 mg/100 ml) | 5 ml |
| 0.528 M MgCl$_2$ (10.73 g/100 ml) | 5 ml |
| 5 M NaCl (292.2 g/l) | 50 ml |
| 0.5% L-Methionine (500 mg/100 ml) | 5 ml |
| micronutrients* | 5 µl |
| *Micronutrients in 25 ml H$_2$O | |
| ZnSO$_4$ (2.88 mg/ml) | 25 µl |
| MnCl$_2$ (1.58 mg/ml) | 250 µl |
| CuSO$_4$ (1.6 mg/ml) | 25 µl |
| CoCl$_2$ (7.14 mg/ml) | 25 µl |
| H$_3$BO$_3$ (2.47 mg/ml) | 250 µl |
| NH$_4$MO$_7$O$_{24}$ (3.71 mg/ml) | 25 µl |

After a week, a culture was obtained which could grow rapidly in the presence of high concentrations of glyphosate in the growth medium (10 mM or higher). Analysis of the EPSPS activity in the extracts of this culture and comparison of its glyphosate sensitivity with that of wild type *E. coli* revealed that the mutant organism had an altered EPSPS. The glyphosate sensitivity of EPSPS of mutant cells was significantly different from that of wild type. This mutant bacterium was designated E. coli 11303 SM-1. The aroA gene encoding EPSPS from this mutant bacterium was isolated as follows.

Isolation of aroA gene encoding EPSPS from E. coli 11303 SM-1: The DNA from this bacterium was isolated (Marmur, J. (1961) J. Mol. Biol. 3:208-218).

The resulting plasmid pMON25 contains the EPSPS coding sequence preceded by unique BamHI and BglII sites, a synthetic ribosome binding site, and unique XbaI and NcoI sites the latter of which contains the ATG translational initiator signal of the coding sequence.

To construct pMON6001, pMON25 was digested with BamHI and mixed with a synthetic DNA fragment containing a partial phage lambda pL sequence (Adams and Galluppi, 1986) containing BamHI sticky ends:

```
5' GATCCTATCTCTGGCGGTGTTGACATAAATACCACTGGCGGTGATACTGAGCACATCG
   GATAGAGACCGCCACAACTGTATTTATGGTGACCGCCACTATGACTCGTGTAGCCTAG
```

Southern hybridization using E. coli K-12 aroA gene (Rogers et al., 1983) as the probe established that the aroA gene in the mutant bacterium was on a 3.5 Kb BglII-HindIII fragment. This fragment was cloned into the vector pKC7 (Rao, R. N. & Rogers, S. G. (1979), Gene, F. Jul. 7, 1982) and the resulting plasmid was used for trans-formation of E. coli. Transformed colonies were screened for their ability to grow in these conditions and were shown to contain the 3.5Kb BglII-HindIII insert by hybridization with the E. coli K-12 aroA gene. This clone was designated pMON9538. An NdeI-EcoRI fragment of this insert which contains greater than 86% of the aroA gene from the mutant bacterium was cloned into an expression vector (pMON6012, a derivative of pMON6001 described below) generating a hybrid EPSPS coding sequence carrying the E. coli K-12 aroA coding sequence of E. coli K-12 and 11303 SM-1. This clone was designated pMON9540. The EPSPS produced by this hybrid aroA gene retained its glyphosate tolerance, suggesting that the mutation conferring glyphosate tolerance to EPSPS in 11303 SM-1 was localized within amino acids 53-427. The E. coli mutant EPSPS gene was incorporated into plant transformation vector with and without a chloroplast transit peptide in the following manner.

Plasmid pMON6001 is a derivative of pBR327 (Soberon et al., 1980) carrying the E. coli K12 EPSPS coding sequence expressed from two tandem copies of a synthetic phage lambda pL promoter. Plasmid pMON6001 was constructed in the following manner. First, pMON4 (Rogers et al., 1983) was digested with ClaI and the 2.5 kb fragment was inserted into a pBR327 that has also been cleaved with ClaI. The resulting plasmid, pMON8, contains the EPSPS coding sequence reading in the same direction as the beta-lactamase gene of pBR327.

To construct pMON25, a derivative of pMON8 with unique restriction endonuclease sites located adjacent to the E. coli EPSPS coding sequence, the following steps were taken. A deletion derivative of pMON4 was made by cleavage with BstEII and religation. The resultant plasmid, pMON7 lacks the 2 kb BstEII fragment of pMON4. Next, a 150 bp HinfI to NdeI fragment which encodes the 5' end of the EPSPS open reading was isolated after digestion of pMON7 with NdeI and HinfI and electroel-tution following electrophoretic separation on an acrylamide gel. This piece was added to the purified 4.5 kb BamHI-NdeI fragment of pMON8 which contains the 3' portion of the EPSPS coding sequence and a synthetic linker with the sequence:

```
5'-GATCCAGATCTGTTGTAAGGAGTCTAGACCATGG
   GTCTAGACAACATTCCTCAGATCTGGTACCTTA
```

The resulting plasmid pMON6001 carries two copies of the synthetic phage lambda pL promoter fragments as direct repeats in the BamHI site of pMON25 in the correct orientation to promote transcription of the EPSPS coding sequence. The BglII-HindIII fragment from pMON6001 which contains the E. coli K-12 aroA gene was inserted into a pEMBL18+ vector and a EcoRI site was inserted at aa27 by site directed mutagenesis. This clone with the new EcoRI site was called pMON653. The NdeI-BglII fragment (which includes the new EcoRI site) from pMON6530 was cloned into the NdeI-BglII digested pMON9540 to give pMON6531.

Plasmid pMON6012 is a simple derivative of pMON6001 created by cleavage of pMON6001 and EcoRI, treatment with large Klenow fragment of E. coli DNA polymerase and ligation. This gave rise to pMON6010 which contains no EcoRI cleavage site. Plamid pMON6012 was then created by digestion of pMON6010 with PvuII and insertion of a synthetic EcoRI linkrr:

```
5'-CCGGAATTCCGG
   GGCCTTAAGGCC
``` into the unique PvuII site near the end of the EPSPS coding sequence.

The 330bp EcoRI fragment of pMON9531 (was cloned into M13 mp9 creating a new plasmid M8017. Site directed mutagenesis was performed to introduce a BglII site in the leader sequence just 5' of the chloroplast transit peptide using the mutagenesis primer

```
5'-CCATTCTTGAAAGATCTAAAGATT-
   GAGGA
```

The mutagenized clone obtained is designated M13 M8020. The BglII-EcoRI fragment was cloned into BglII-EcoRI digested pMON530 creating pMON536. pMON530 is a pMON505 derivative (Horsch & Klee, 1985) carrying the 35S-NOS cassette created by transferring the 2.3 kb StuI-HindIII fragment of pMON316 into pMON526. Plasmid pMON526 is a simple derivative of pMON505 in which the SmaI site was removed by digestion with XmaI, treatment with Klenow polymerase and ligation. The resultant plasmid, pMON530 (FIG. 2) retains the properties of pMON505 and the 35S-NOS expression cassette now con-tains a unique cleavage site for SmaI between the promoter and polyadenylation signals. The EcoRI fragment containing the aroA gene from pMON6031 was cloned into the EcoRI site of pMON536 creating pMON542.

The BglII-EcoRI fragment of pMON9540 which encodes the hybrid K12-SM1 EPSPS without the CTP was cloned into the BglII and EcoRI sites of pMON530 to create pMON8078.

Transformation of tobacco cells using pMON542 (construct with CTP) as previously described in Example 3 resulted in glyphosate resistance. Conversely, transformation of tobacco with pMON8078 (construct without CTP) failed to confer glyphosate resistance.

Example 9: Gly$^R$ Potato Cells

Potato—Shoot tips of virus-free Russet Burbank are subcultured on media containing MS major and minor salts, 0.17 g/l sodium dihydrogen phosphate, 0.4 mg/l thiamine hydrochloride, 0.1 g/l inositol, 3% sucrose, 1.5 g/l Gelrite TM (Kelco, Co ) at pH 5.6. Cultures are grown at 24C in a 16 hour photoperiod. Shoots are used approximately 3-4 weeks after subculturing. Stem internodes are cut into approximately 8 mm lengths and split lengthwise, then the cut surface is smeared with Agrobacterium carrying binary vector pMON542 and helper plasmid pTiT37-SE which had been streaked on an LB agar plate and grown for a few days. Stem sections are placed cut side down on the surface of the medium containing MS salts, MS organics, 3% sucrose, 2.25 mg/l BA, 01186 mg/l NAA, 10 mg/l GA, 1.5 g/l Gelrite at pH 5.6. After 4 days, the stem explants are transferred to the same medium but with carbenicillin at 500 mg/l and kanamycin as the selective agent at 0 or 300 mg/l. Two weeks after inoculation, the explants are moved onto medium of the same composition but without NAA. Kanamycin at 300 mg/l was sufficient to prevent swelling and callusing of the infected explants without killing the tissue. The transformed tissue appears as small outgrowths usually on the end of the explant. Transformed tissue exhibits substantial resistance to glyphosate.

Example 10: Gly$^R$ Sunflower Cells

The following procedures are utilized to obtain transformed sunflower tissue and shoots. Tumors are incited on sterile sunflower seedlings. Sunflower seeds are surface sterilized with 40% Chlorox and sterile distilled water rinses. The seeds are germinated on an agar medium containing B5 salts, 0.5% sucrose and 0.8% agar. Seven-day old seedlings are inoculated with overnight cultures of Agrobacterium strains carrying pTiB6S3-SE by scoring the internode or stabbing the internode with a syringe and using another syringe to introduce the bacteria into the wound. Tumors form in 2-3 weeks. The tumors are removed from the seedlings and grown independently on MS medium without hormones. Transformed callus and shoots are also obtained following a different procedure. Seeds are surface sterilized and placed on the germination medium above. Germination is carried out in the light for 10 days. Hypocotyl segments, 2-3 mm are, excised and inoculated with Agrobacterium strains containing engineered constructs. The hypocotyls are co-cultured for 2 days on a medium containing MS salts and vitamins, 5 g/l KN03, 100 mg/l inositol, 40 mg/l adenine sulfate, 500 mg/l casamino acids, 1 mg/l NAA, 1 mg/l BA, 0.1 mg/l GA3, 30 mg/l sucrose and 8 gm/l agar. After co-culture, the hypocotyls are placed on the same medium but containing 300 mg/l kanamycin and 500 mg/l carbenicillin. After 2 weeks, the hypocotyls inoculated with strains containing the kanamycin resistance gene produce callus and regenerates on medium containing kanamycin while other hypocotyls do not.

*A. tumefaciens* containing binary vectors pMON546 and helper plasmid pTiB6S3-SE are used to produce tumors and callus and regenerated plants. The tumors exhibit tolerance to glyphosate at concentrations which bleach and kill control tumors which do not contain the glyphosate resistance gene. Non-tumorous callus likewise show tolerance to levels of glyphosate which kill callus without the glyphosate resistance gene. Transformed sunflower plants demonstrate tolerance to glyphosate sprayed at concentrations which kill wild type plants.

Example 11: Gly$^R$ Petunia Plants

Transformed petunia plants were produced by regeneration from the transformed leaf disks of Example 2, by the procedure described in Horsch et al 1985. The transformed plants obtained contained the pMON546 vector, described hereinbefore, which contains the CaMV 35S promoter fused to the wild-type petunia EPSPS gene.

Four individual representative transgenic seedlings were selected, grown and tested in the testing procedure described below, along with four individual non-transformed (wild-type) petunia seedlings.

The plants were grown in a growth medium in a growth chamber at 26° C. with 12 hours of light per day. The plants were fertilized weekly with a soluble fertilizer and watered as needed. The plants were sprayed at a uniform and reproducible delivery rate herbicide by use of an automated track sprayer.

The glyphosate solution used was measured as pounds of glyphosate acid equivalents per acre, mixed as the glyphosate isopropylamine salt, with an ionic surfactant.

Four individual wild-type (non-transformed) petunia plants were selected for use as control plants. Four individual transformed plants containing the pMON546 vector were selected by kanamycin resistance as described in Horsch et al 1985.

The control plants and the transformed plants were sprayed with the isopropylamine salt of glyphosate at the application level listed in Table 2 below; the experimental results obtained are also summarized in Table 2.

TABLE 2

| Plant Response to Glyphosate Spraying | | |
|---|---|---|
| Plant Type | Glyphosate Dose* | Visual Appearance |
| Control | 0.4 #/acre | plants showed rapid chlorosis and bleaching, wilted and died |
| Control | 0.8 #/acre | completely dead, plants showed very rapid chlorisis and bleaching, wilted and died |
| Chimeric EPSPS transformants | 0.8 #/acre | growing well, slight chlorisis in new leaves which are growing with normal morphology, plants appear healthy and started to flower |

*Acid Equivalent

As indicated in Table 2, the control plants were killed when sprayed with 0.4 pounds/acre of glyphosate. In contrast, the petunia plants which were transformed were healthy and viable after spraying with 0.8 pounds/acre. The transformed plants are more resistant to glyphosate exposure than the non-transformed control plants.

Example 12: Gly$^R$ Tomato Plants

Transformed tomato plants, VF36 variety are produced from sterile seedlings as described below.

Sterile seedlings of VF36 tomato are grown on water agar. Hypocotyls and cotyledons are excised and cultured for 2 days on MS medium containing B5 vitamins, 30 g/l sucrose and 1 mg/l benzyladenine and 0.1 mg/l indole acetic acid. The seedlings are then infected with the *A. tumefaciens* vector containing the chimeric EPSPS gene described in Example 2, by immersing for about 30 seconds in a culture of *A. tumefaciens* containing the chimeric EPSP synthase gene that had been diluted to $10^7$ bacteria/ml. Explants are obtained by cutting sections from the seedlings. The explants are blotted dry and incubated as described previously in Example 2 except that the medium contains only 10% of standard concentration of MS salts. After 2 days of coculture, the explants are transferred to selective medium containing 100 ug/ml kanamycin. Transformed tomato plants grow from the explants. Leaves from these plants are tested for glyphosate resistance using a leaf callus assay described below. Tomato leaf fragments from plants containing vector alone (pMON200) or the pMON546 chimeric EPSPS gene are incubated on callus medium described above containing 0.5 mM glyphosate. After 10 days the control leaves are completely inhibited and showed no signs of callus growth; the leaves from plants transformed with the chimeric EPSPS gene vector produced callus.

Example 13: Gly$^R$ Tobacco Plants

Transformed tobacco plants (Samsun variety) were produced and grown by the method described in Example 4, substituting transformed tobacco leaf disks for transformed petunia leaf disks.

Tobacco plants were tested for glyphosate resistance using the method described for tomato plants in Example 5. Tobacco leaf fragments from plants containing vector alone (pMON200) or the pMON546 chimeric EPSPS gene were incubated on callus medium containing 0.5 mM glyphosate.

After 10 days the control tobacco leaves were completely inhibited and showed no signs of callus growth; the leaves from plants transformed with the chimeric EPSPS that the chimeric petunia EPSPS gene confers glyphosate resistance to tobacco plants.

Example 14: Isolation of Petunia EPSPS Genomic Clone

In order to isolate the entire petunia EPSPS gene, the library of petunia genomic DNA was constructed as described in Example 1-G. Briefly, the chromosomal DNA from the MP4-G cell line was digested with BamHI and cloned into a phage vector, λMG14, to create a library. As described in Example 1-G, one phage clone λF7 was isolated which contains a 4.8 kb BglII fragment that was complementary to pMON9531 cDNA clone. To isolate the remainder of the gene, the genomic library was screened again using as probe the 1.6 kb cDNA insert from pMON9556. The plating of the library and the hybridization procedures were done as described in Example 1-G. Several positive signals were obtained. One isolate was selected for further analysis and was designated as the λF10 phage clone.

Figure 6:
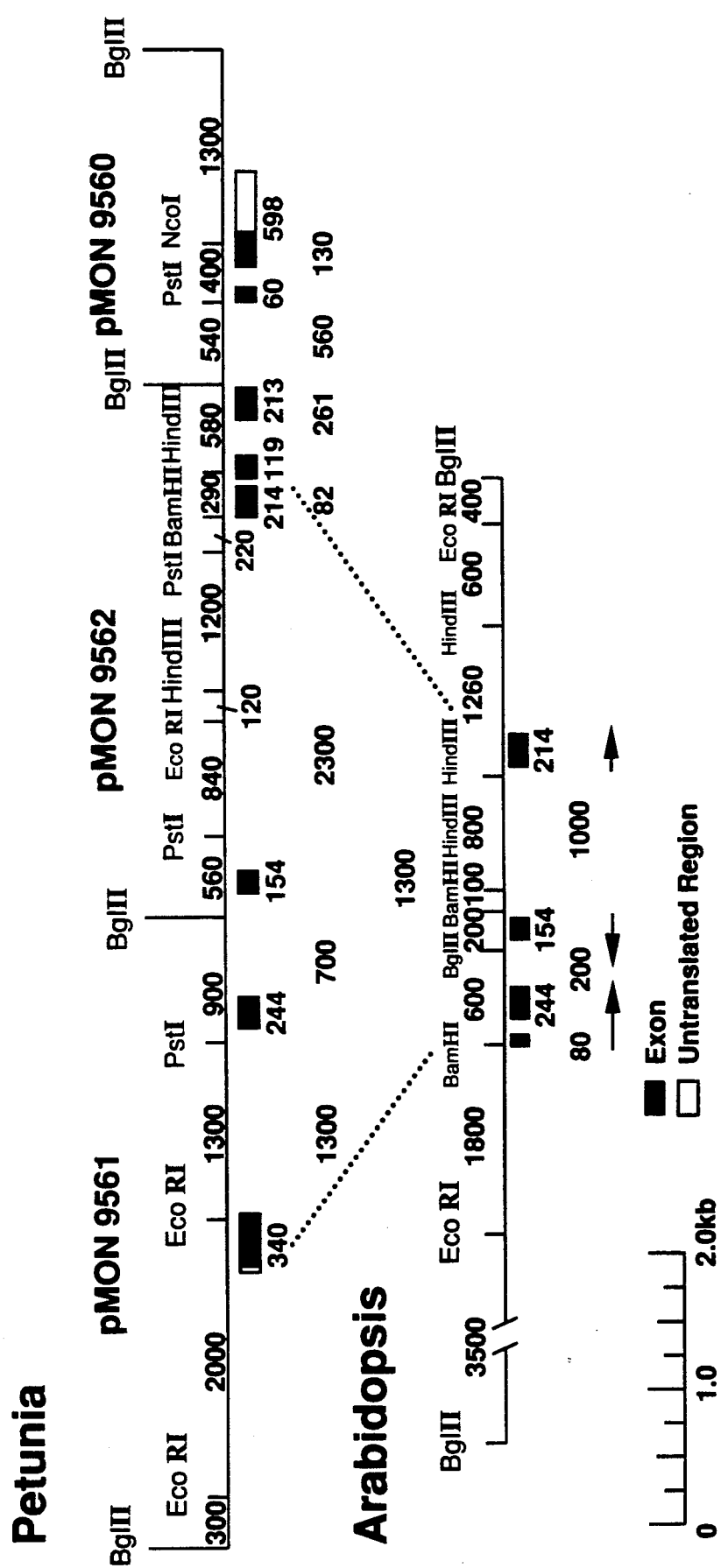
FIG. 6 shows the restriction maps for the EPSPS gene of Petunia and Arabidopsis.

The DNA from λF10 was digested separately with BamHI, BglII, EcoRI and HindIII. The DNA was hybridized with nick-translated EPSPS sequences from pMON9531 and pMON9556 in a Southern blot procedure. This indicated that the complementary sequences from λF10 were on 4.8 kb, 2.0 kb and 3.8 kb BglII fragments. DNA sequence analysis of these fragments indicates that these three fragments together contain the entire gene which spans approximately 9 kb of petunia DNA and is interrupted by seven introns (FIG. 6). The promotor fragment of the EPSPS gene contained in the genomic clone, λF10, can be used to express the chimeric EPSPS cDNA or genomic sequences. The fragments containing the introns may also be used to construct additional chimeric EPSPS genes to obtain enhanced levels of the mRNA.

Example 15: Isolation of *Arabidopsis thaliana* Genomic Clone

An *Arabidopsis thaliana* genomic bank was constructed by cloning size fractionated (15–20 kb), MboI partially digested DNA into BamHI cut lambda EMBL3. Approximately 10,000 plaques of phage from this library were screened with a nick-translated petunia EPSPS probe (pMON9566). A strongly hybridizing plaque, E1, was purified. Southern blots of the EPSPS probe to phage DNA digests identified two fragments which hybridized very strongly. The first of these was a 1.0 kb HindIII fragment and the other was a 700 bp BamHI fragment. Both of these fragments were subcloned into pUC119 and the DNA sequences of the inserts determined.

The sequence data indicated that the phage did contain the Arabidopsis EPSPS gene. The enzyme is highly homologous to the petunia enzyme over the area for which sequence was available. The BamHI fragment was used as a hybridization probe against the phage and Arabidopsis genomic DNA to identify restriction endonuclease fragments suitable for cloning the entire gene. Two BglII fragments of 6.0 and 3.2 kb were identified from the E1 phage clone which, together, contain the entire EPSPS gene. FIG. 6 summarizes the organization of the Arabidopsis clone and compares it to the organization of the Petunia EPSPS gene.

The DNA encoding the amino terminus of the protein is within the 6.0 kb BglII fragment. The exact translational start site can be determined by comparison of the amino acid sequence deduced from the nucleotide sequence to that of the petunia enzyme. Site directed mutagenesis can then be used to introduce a unique EcoRI site immediately upstream of the translational start codon. The entire gene can then be isolated as an EcoRI fragment. This EcoRI fragment can be inserted into the expression vector, pMON530, and the resulting vector used to overexpress the Arabidopsis EPSPS enzyme in plants.

Example 16: Isolation of Tomato EPSP cDNA Clone

A cDNA library was constructed from RNA isolated from mature pistils of tomato (*Lycopersicum esculentum* variety VF36) by the methods of Huynh et. al (in: DNA Cloning Techniques: A Practical Approach, IRL Press, D. Glover ed., 1985) and Gubler and Hoffman (Gene 25:263–269, 1985). The library was plated on *E. coli* strain BNN102 and filter replicas were made. The filters were hybridized with the 1.9 kb BglII/ClaI fragment of pMON9563 that had been labeled with $^{32}P$ (Feinberg and Vogelstein (Anal. Biochem. 132:6–13, 1983). Hybridizing plaques were isolated and rescreened by the same method to verify the presence of EPSPS cDNA. The full length tomato EPSPS cDNA was present on two EcoRI fragments of 250 and 1700 bp in one of the cDNA clones (Pl). The 250 bp fragment was cloned into the EcoRI site of pUC119 forming pMON9596. The 1700 bp fragment was cloned into pUC19 forming pMON9589. The insert of pMON9596 was sequenced using a dideoxy sequencing kit purchased from Amersham to determine the sequence surrounding the start codon to facilitate mutagenesis. A BglII site was engineered 13 bases upstream of the translation start codon of pMON9596 by the method of Kunkel (Proc. Natl. Acad. Sci. USA 82:488–492, 1985) using the chemically synthesized oligonucleotide:

GCCATTTCTTGTGAAAAAGATCTT-CAGTTTTC

Figure 7:
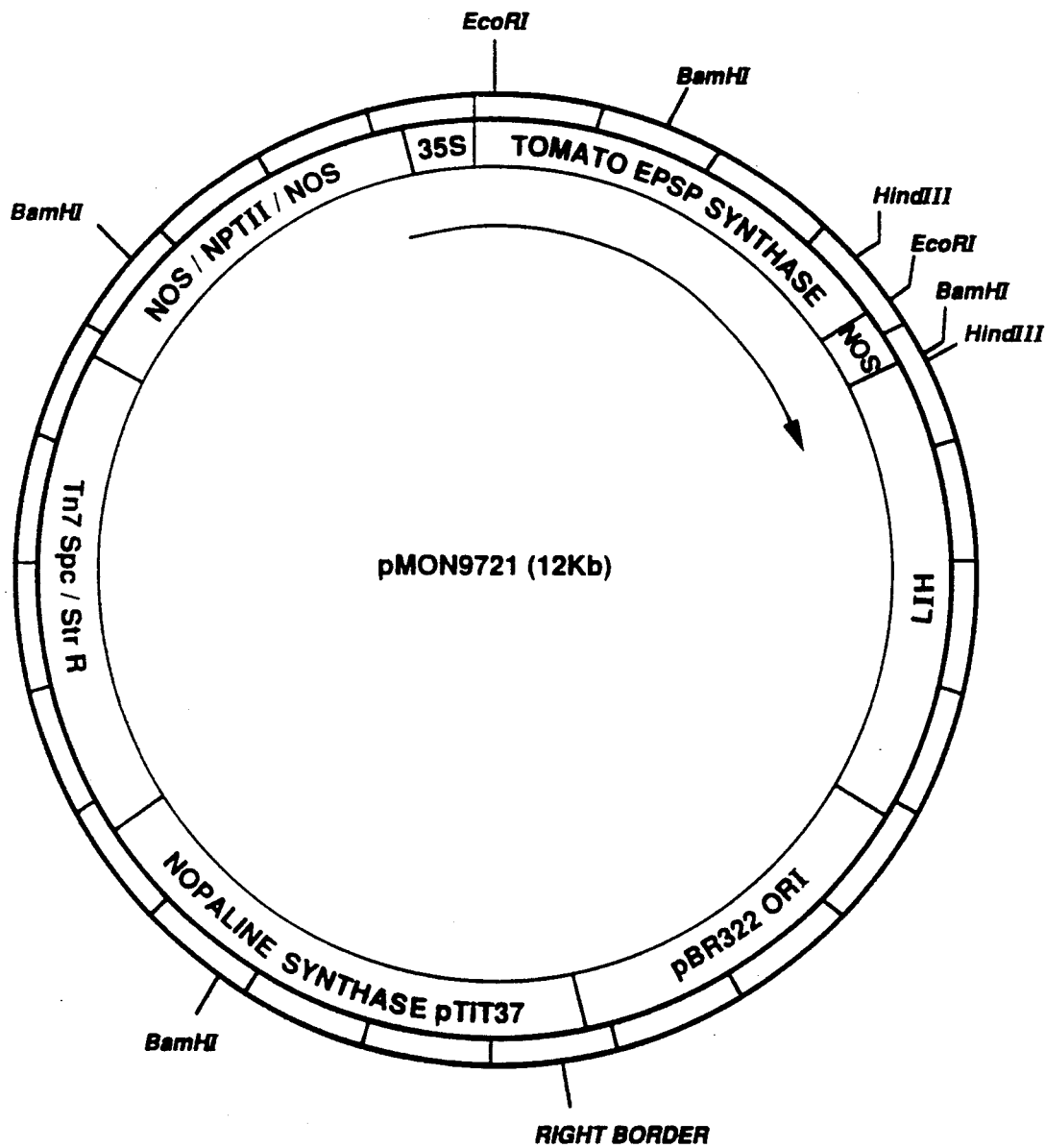
FIG. 7 shows the plasmid map for pMON9721.

The insert of the resulting plasmid, pMON9710, was sequenced to verify the correct mutation. The 70 bp BglII/EcoRI fragment of pMON9710 was inserted into pMON316 which had been digested with BglII and EcoRI pMON316 which had been digested with BglII and EcoRI creating pMON9720. The 1700 bp EcoRI fragment of pMON9589 was inserted into the EcoRI site of pMON9720 in the correct orientation to reconstitute the EPSPS coding region resulting in pMON9721 (see FIG. 7).

This plasmid was inserted into *A. tumefaciens* cells which contained a helper plasmid, pGV3111-SE. The helper plasmid encodes certain enzymes which are necessary to cause DNA from pMON9721 to be inserted into plant cell chromosomes. It also contains a kanamycin resistance gene which functions in bacteria. *A. tumefaciens* cells containing pMON9721 are used in plant transformation experiments to produce glyphosate resistant cells and plants as previously described in Example 12.

Example 17: Isolation of *Brasicca napus* cDNA Clone

Total RNA was isolated from *Brassica napus* (cultivar Westar) flowers as follows. Flowers were frozen in liquid nitrogen. After liquid nitrogen had evaporated, flowers were homogenized in extraction buffer (1% tris-isopropylnapthalene sulfonic acid, 6% p-aminosalicylic acid, 100 mM Tris-HCl, pH 7.6, 50 mM EGTA, pH 7.5, 100 mM NaCl, 1% SDS and 50 mM 2-mercaptoethanol) and then extracted with equal volume of a 1:1 mixture of phenol/chloroform. The nucleic acids in the aqueous phase were precipitated with ethanol. The precipitate was dissolved in water and the RNA was precipitated twice with LiCl to a final concentration of 2M. The final RNA pellet was dissolved in water and the RNA was precipitated with ethanol. PolyA RNA was selected by olig-dT cellulose chromatography. The yield of polyA RNA was 1.0 μg/gram of flowers.

The library was constructed using polyA RNA from *Brassica napus* flowers and the method used is described in Example 16. The yield in the library was 90,000 plaques/3 μg polyA RNA. The library was plated at a density of 5000 plaques/plate. The phage DNA was transferred to nitrocellulose filters. The filters were hybridized under low stringency in 35% formamide, 5×SSC, 300 μg/ml tRNA, 0.1% SDS at 37° C. The insert from pMON9556 was labeled with $^{32}P$ by nick-translation and added to the hybridization solution at $2\times10^6$ cpm/ml. The filters were washed in 2×SSC at room temperature twice for 15 min each and once at 37° C. for 30 min. A number of positively hybridizing phage were obtained. These phage were picked and rescreened twice at lower plaque densities. The positively hybridizing phage were selected and those containing a full length *B. napus* EPSPS cDNA clone were chosen for further analysis. The full length *B. napus* EPSPS cDNA clone will be modified and inserted into a plant expression vector, pMON530, to create a chimeric CaMV 35S/*B. napus* EPSPS gene.

Example 18: Petunia EPSPS Chloroplast Uptake Requires CTP Sequence

A full-length cDNA clone of EPSPS from *P. hybrida* was obtained as described in Example 1. This cDNA clone contains 27 nucleotides of the 5' untranslated leader, 1.5 kb which codes for the 72 amino acid transit peptide plus 444 amino acids of the mature enzyme, and 0.4 kb of the entire 3' flanking sequence The full-length EPSPScDNA was cloned as a 2.1 kb BglII-SAlI fragment into the BamHI/SalI sites of the plasmid pGEM1 to give plasmid pMON6140 and into PGEM2 to give pMON6145. The EPSPS coding region is transcribed 5' to 3' from the T7 and SP6 promoters respectively.

Plasmid DNA (pMON6140 and pMON6145) containing the full-length EPSPS cDNA was linearized at a unique Pvu I site located in the 3' untranslated region. The linearized plasmid DNA was transcribed in vitro (uncapped) with SP6 and T7 polymerase essentially as described in Krieg et al, 1984. The standard reaction buffer contained 40 mM Tris-HCl (pH 7.9), 6 mM $MgCl_2$, 10 mM dithiothreitol, 2 mM spermidine, 80U RNasin ribonuclease inhibitor, 0.5 mM each of ATP, GTP, CTP and UTP, in a final reaction volume of 100 μl. The final RNA pellet was resuspended in 20 μl of sterile water and stored at −80° C. A standard translation reaction contained 100 μl of nuclease-treated rabbit reticulocyte lysate, 5.7 μl of a 19-amino acid mixture (minus methionine) at 1 mM each, 5.7 μl of RNA (total RNA transcripts derived from 0.63 μg of plasmid DNA), 16 μl RNasin (20U/μl) ribonuclease inhibitor, and 58.3 μl of [35S]methionine (14–15mCi/ml). The in vitro translation reaction was run at 30° C. for 90 min. The translation products were stored frozen at −80° C.

Intact chloroplasts were isolated from lettuce (*Latuca sativa*, var. *longifolia*) by centrifugation in Percoll/ficoll gradients as modified from Bartlett et al (1982). The final pellet of intact chloroplasts was suspended in 0.5 ml of sterile 330 mM sorbitol in 50 mM Hepes-KOH, pH 7.7, assayed for chlorophyll (Arnon, 1949), and adjusted to the final chlorophyll concentration of 4 mg/ml (using sorbitol/Hepes). The yield of intact chloroplasts from a single head of lettuce was 3–6mg chlorophyll. These chloroplasts were deemed homogeneous based on phase contrast and transmission electronmicroscopy.

A typical 300 μl uptake experiment contained 5 mM ATP, 8.3 mM unlabeled methionine, 322 mM sorbitol, 58.3 mM Hepes-KOH (pH 8.0), 50 μl reticulocyte lysate translation products, and intact chloroplasts from *L. sativa* (200 μg chlorophyll). The uptake mixture was gently rocked at room temperature (in 10×75 mm glass tubes) directly in front of a fiber optic illuminator set at maximum light intensity (150 Watt bulb). Aliquots of the uptake mix (50–125 μl) were removed at various times and fractionated over 100 μl silicone-oil gradients (in 150 μl polyethylene tubes) by centrifugation at 11,000×g for 30 sec. Under these conditions, the intact chloroplasts form a pellet under the silicone-oil layer and the incubation medium (containing the reticulocyte lysate) floats on the surface. After centrifugation, the silicone-oil gradients were immediately frozen in dry ice. The chloroplast pellet was then resuspended in 50–100 μl of lysis buffer (10 mM Hepes-KOH pH 7.5, 1 mM PMSF, 1 mM benzamidine, 5 mM ε-amino-n-caproic acid, and 30 μg/ml aprotinin) and centrifuged at 15,000×g for 20 min to pellet the thylakoid membranes. The clear supernatant (stromal proteins) from this spin, and an aliquot of the reticulocyte lysate incubation medium from each uptake experiment, were mixed with an equal volume of 2×NaDodSO4-PAGE sample buffer for electrphoresis (see below).

NaDodSO4-PAGE was carried out according to Laemmli (1970) in 12% (w/v) acrylamide slab gels (60 mm×1.5 mm) with 3% (w/v) acrylamide stacking gels (5 mm×1.5 mm). The gels were fixed in 30% methanol and 10% acetic acid, dried under vacuum, and taken for direct autoradiography with Kodak XAR-5 X-ray film. Quantitation of bands on the X-ray film was performed using a Hoefer GS-300 scanning densitometer interfaced with a Spectra-Physics SP4100 recording/computer integrator.

To verify that precusor EPSPS (+CTP) is taken up and processed by chloroplasts, the total translation products containing [35S]methionine-labeled pre-EPSPS were incubated with freshly isolated, intact chloroplasts from L. sativa. The pre-EPSPS (+CTP) was rapidly translocated into chloroplasts and cleaved to the mature EPSPS of $M_r$ α48 kDa. The NaDodSO4-PAGE autoradiograph revealed the disappearance of the precursor EPSPS from the incubation medium, and the subsequent appearance of a lower molecular weight, mature form in the chloroplast fraction. Some of the mature EPSPS was also present in the incubation medium at 15 minutes due to chloroplast lysis. Post-uptake treatment of the incubation mixture with trypsin and chymotrypsin showed that the pre-EPSPS in the incubation medium was completely degraded, whereas the mature EPSPS in the chloroplast fraction was fully protected. These results indicate that EPSPS was translocated across the chloroplast envelope into a protease inaccessible space. Furthermore, subfractionation of the reisolated chloroplasts indicated that the mature EPSPS was localized in the stromal, as opposed to thylakoid, fraction. Based on nucleotide sequence, the predicted molecular weight for the mature P. hybrida EPSPS is 47,790 daltons. The $M_r$ α48 kDa polypeptide localized in the reisolated chloroplast fraction co-migrated during NaDodSO4-PAGE with the purified mature EPSPS of P. hybrida.

In order to show that the CTP is required for uptake, the mature enzyme (lacking the CTP) is isolated from the chloroplast stroma after an initial 15 minute uptake experiment. A mixture of stromal proteins (containing the labeled mature enzyme) was diluted with unlabeled reticulocyte lysate and used in a second uptake experiment with intact chloroplasts. The mature EPSPS (lacking the CTP) was not translocated into chloroplasts, or bound to the outer-envelope membrane, during a 15 minute incubation. As a control experiment, we found that the rate of uptake of pre-EPSPS into chloroplasts was unaffected by the addition of stromal proteins to the incubation mixture. From these data it is concluded that the CTP of EPSPS is required for uptake of the enzyme into chloroplasts.

Example 19: CTP of Petunia EPSPS Facilitates

The following EPSPS experiments show that the CTP can target a heterologous protein to the stroma compartment. The 72-amino-acid transit peptide of EPSPS was fused to the mature ssRUBISCO from wheat. The mature wheat ssRUBISCO cDNA (Broglie et al 1983) was obtained as an SphI/PstI fragment of ~0.6 kb. This SphI/PstI fragment contains the entire mature wheat ssRUBISCO coding region of 128 amino acids (beginning at the N-Terminal methionine) and 200 bp of the 3' untranslated region. The mature ssRUBISCO cDNA fragment was fused behind the P. hybrida EPSPS CTP cDNA fragment. This fusion was done by joining an EcoRI/SphI fragment of pMON6242 with the wheat ssRUBISCO cDNA. The construct pMON6242 is a derivative of pMON6140 and contains P. hybrida EPSPS with an engineered consensus cleavage site for ssRUBISCO. The cleavage site of pMON6140 EPSPS (ser-val-ala-thr-ala-gln/lys) was changed to gly-gly-arg-val-ser-cys/met in pMON6242. This change introduces an in-frame SphI site which allows CTP switching between ssRUBISCO and EPSPS. The construct pMON6242 has previously been cloned into pGEM-2 and shown to give a chimeric precursor enzyme which is transported into chloroplasts in vitro and proteolytically processed in the correct fashion.

The EcoRI/SphI fragment from pMON6242 was fused to the SphI site from wheat ssRUBISCO and cloned into plasmid pIBI to give pMON6149. In vitro transcription/translation of pMON6149 gave a single polypeptide of the predicted molecular weight for the fusion protein (~23 kD). Chloroplast import assays in vitro showed that the chimeric protein was transported into the stroma and proteolytically cleaved to a final product of ~15 kD (the ssRUBISCO has a molecular weight of 15 kD).

These results show that the EPSPS CTP alone confers sufficient information to target a heterologous protein to the chloroplast stroma.

Example 20

An A. thaliana meristematic promoter region was tested for its ability to confer improved glyphosate tolerance through enhanced expression of tolerant EPSP synthase in tissues predicted to be more sensitive to glyphosate's deleterious effects. 4 kb BamHI fragment from pMON648 containing the A. thaliana promoter region was inserted into the BamHI site of pUC119 to create pMON1575. A BglII site was then introduced into pMON1575 at the junction of the A. thaliana promoter-leader sequence and its corresponding coding sequence by site directed mutagenesis to create pMON1576. The oligonucleotide primer used for this mutagenesis consisted of the following sequence (5'-3'):

GAAAGGAGACATAGATCTTTGTGTGTG

The underlined nucleotides were inserted to create the BglII site. The 2.4 kb BglII-StuI fragment from pMON1576 was used as the A. thaliana promoter in this example. A chimeric gene consisting of the isolated A. thaliana promoter, variant genomic clones of the A. thaliana EPSP synthase coding region, and the 3' non-translated region of the pea ribulose bisphosphate carboxylase small subunit E9 gene (E9 3') (Coruzzi et al.

1984, and Morelli et al. 1985) was made for this purpose. First, an expression cassette containing the *A. thaliana* promoter, several unique restriction sites, and the E9 3' was made by inserting the 2.4 kb BglII-StuI fragment from pMON1576 into pMON921 digested with BglII and HincII to create pMON1581. A variant *A. thaliana* EPSP synthase coding region which contains two codon changes and encodes a glyphosate tolerant form of the enzyme from pMON982 was then inserted as a filled in ClaI-EcoRI fragment into the StuI site of the expression cassette of pMON1581 to create pMON989. This variant *A. thaliana* EPSP coding sequence is from a genomic clone and has a glycine to alanine substitution at position 101 and an aspartate for glycine substitution at position 144 of the mature protein. The isolation of this gene and its use is described in the co-pending, commonly assigned patent application entitled "Glyphosate-Tolerant 5-Enolpyruvyl-3-phosphoshikimate Synthases" filed on Jul. 17, 1989 and having Ser. No. 07/380,963 which is hereby incorporated by reference hereto.

Figure 8:
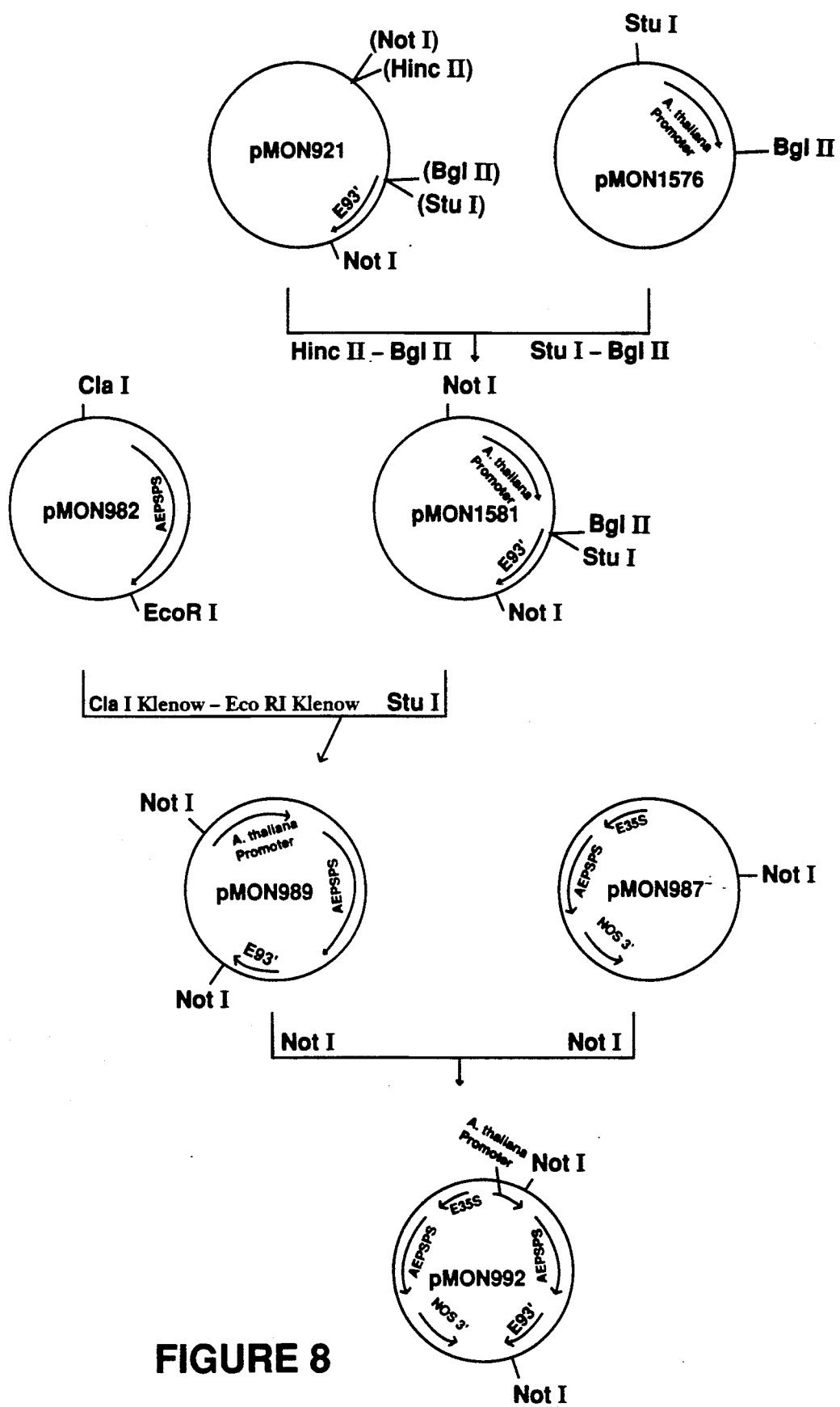
FIG. 8 shows a flow diagram illustrating the formation of pMON992.
Figure 9:
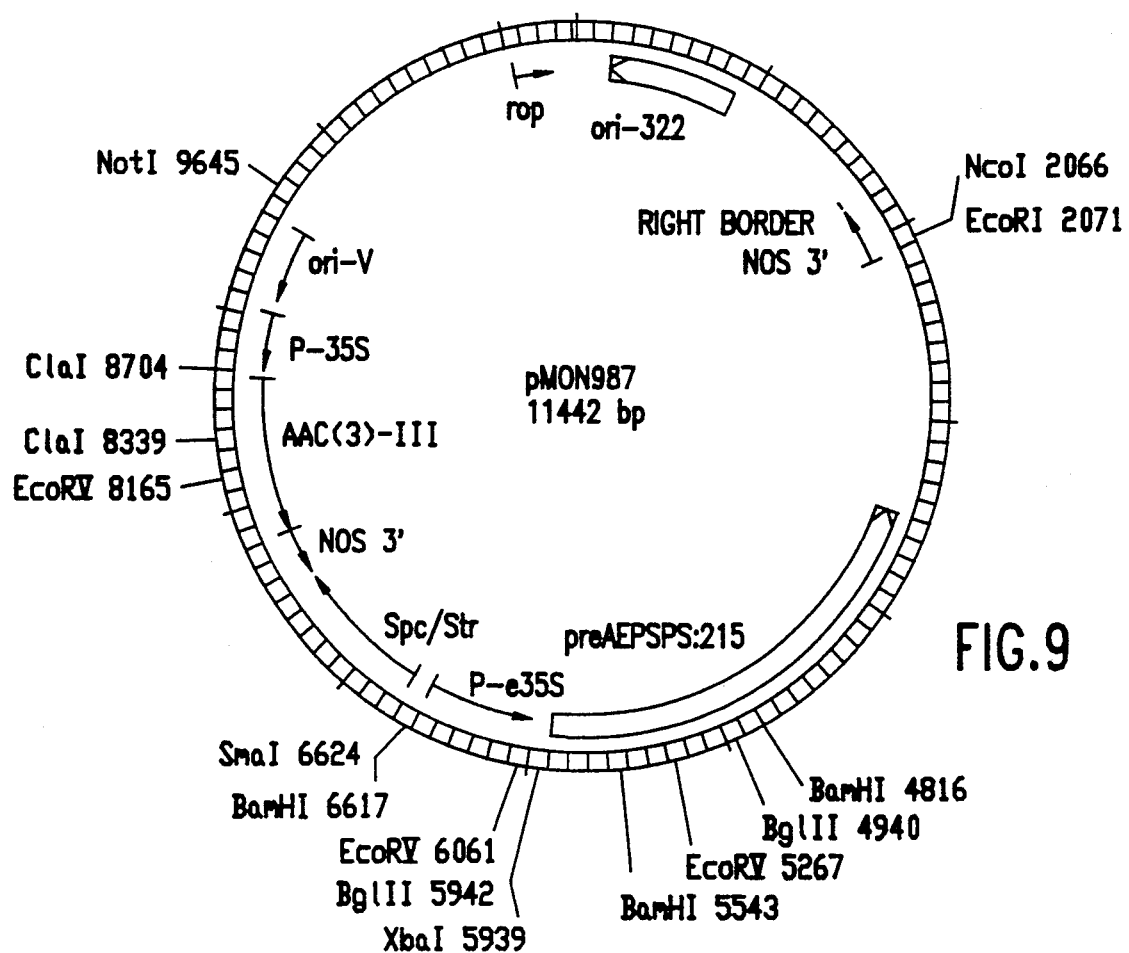
FIG. 9 shows a map of pMON987.
Figure 10:
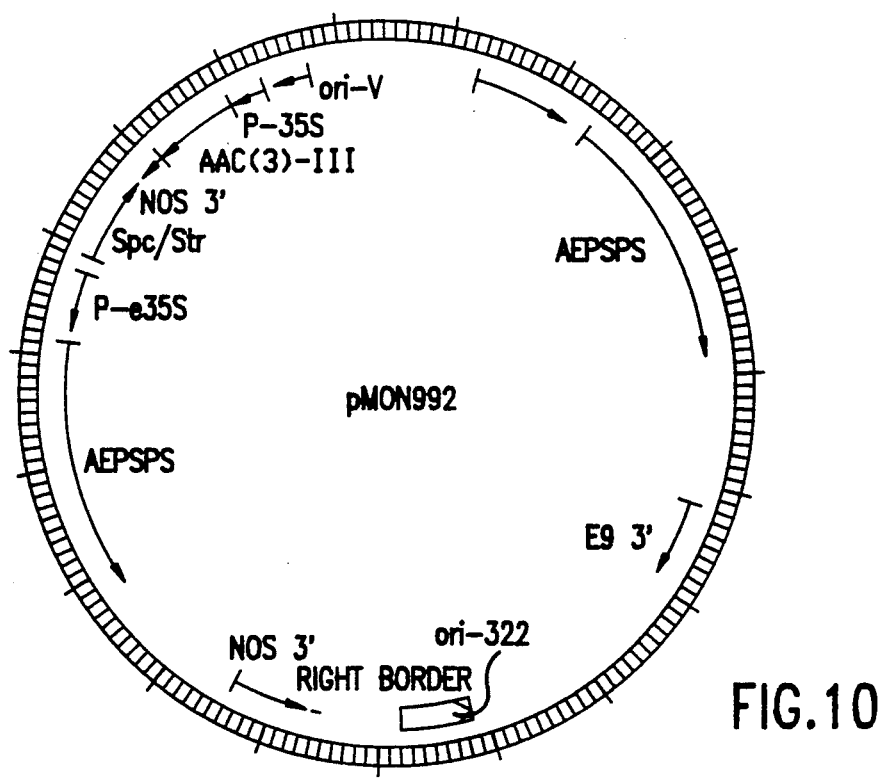
FIG. 10 shows a map of pMON992.

The chimeric gene from pMON989 was inserted as a NotI fragment into the NotI site of pMON987 to create pMON992. A flow diagram illustrating the construction of pMON992 is shown in FIG. 8. Plasmid maps of pMON987 and pMON992 are shown in FIG. 9 and FIG. 10, respectively. The pMON992 construct is made up of the following segments of DNA in addition to the chimeric gene from pMON989. The first is the 3.1 kb SalI to PvuI segment of pBR322 (ori-322) which provides the origin of replication for maintenance in *E. coli* and the bom site for the conjugal transfer into the *A. tumefaciens* cells. The next segment is the 0.36 kb PvuI to BclI fragment from pTiT37 that carries the nopaline-type T-DNA right border (Fraley et al. 1985). It is joined to a 4.7 kb chimeric gene consisting of the enhanced CaMV 35S promoter (Kay et al. 1987), a variant *A. thaliana* EPSP synthase coding region (the same as described for pMON989 above), and the NOS 3' polyadenylation signal. The next segment is a 0.93 kb fragment (AvaI to an engineered EcoRV site) isolated from transposon Tn7 that encodes bacterial spectinomycin/streptomycin resistance (Spc/Str), and is a determinant for selection in *E. coli* and *Agrobacterium tumefaciens*. This is joined to the 1.5 kb segment of DNA encoding a chimeric gentamicin resistance gene which permits selection of transformed plant cells. The chimeric gene (P-35S/AAC(3)-III/NOS 3') consists of the CaMV 35S promoter, the gentamicin-3-N-acetyltransferase type III gene (AAC(3)-III) (Hayford et al. 1988), and the NOS 3' polyadenylation signal. The last segment is the 0.75 kb ori-V containing the origin of replication from the RK2 plasmid.

Both pMON987 and pMON992 were mobilized into the *Agrobacterium tumefaciens* strain ACO using the triparental conjugation system (Ditta et al. 1980). Both were then transformed into *Nicotiana tabacum* and *Brassica napus* plants as previously described.

The transgenic, differentiated plants obtained containing the variant EPSP synthase gene as described above were analyzed for resistance to glyphosate. The transgenic plants containing the Arabidopsis EPSP synthase gene (as described) directed by the *Arabidopsis thaliana* promoter as also described above contained pMON992 while those plants containing the Arabidopsis EPSP synthase gene driven only by the enhanced CaMV35S promoter contained pMON987. These transgenic plants were planted and the seed from the R° plants harvested, threshed and dried before planting for a glyphosate spray test. The progeny were planted in 4-inch square pots of Metro 350 and three types of slow release fertilizers. A goal of twenty seedlings from each R° plant is desirable for testing. Germination frequency is usually high but overplanting ensures that twenty seedlings are present. The plants were thinned down by selecting the twenty most vigorous and erect seedlings seven to ten days after planting. A negative control (non-transformed, "Westar" variety) was planted at the same time to maintain quality and display the results. The plants were maintained and grown in a greenhouse environment. A sixteen-hour photoperiod and a temperature of 21° C. (day) and 15° C. (night) was maintained. Water soluble Peters Pete Lite fertilizer with an analysis of 20-19-18 was applied once per week or as needed.

Two plants from each R° progeny were not sprayed and served as controls to compare and measure the glyphosate tolerance. When the remaining plants reached the six to eight leaf stage, usually 20 to 28 days after planting, glyphosate was applied at a rate equivalent to 0.28 Kg/ha. Low rate technology using low volumes has been adopted. A volume of ten imperial gallons for 0.28 Kg/ha of glyphosate is standard in field tests. A laboratory test sprayer had been calibrated to deliver a consistent rate equivalent to field conditions.

Figure 11:
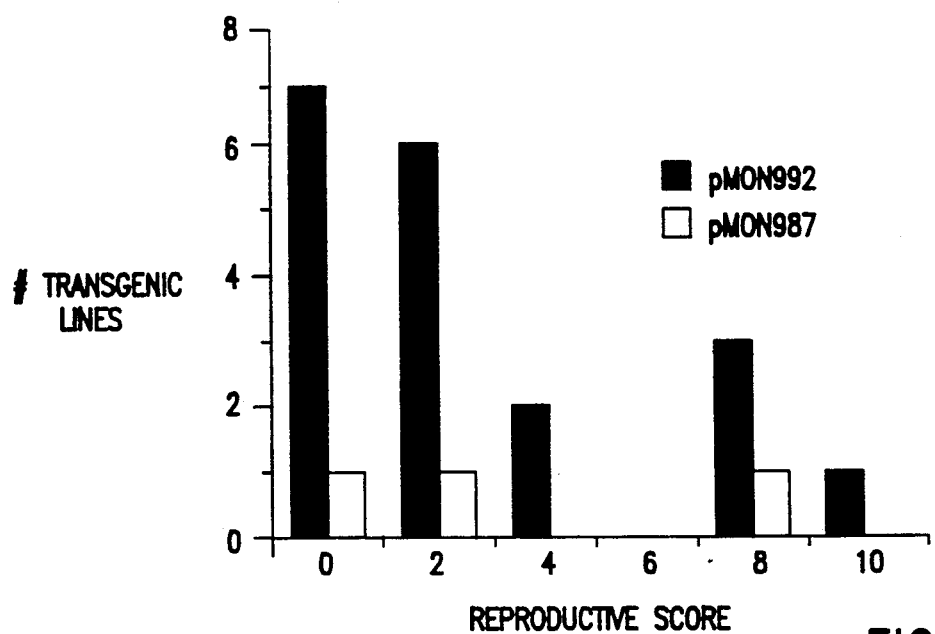
FIG. 11 shows the reproductive scores after glyphosate application of transgenic plants containing a variant EPSP synthase gene under the control of an *Arabidopsis thaliana* promoter region that confers high expression in meristematic tissue or an EPSP synthase gene only under the control of the enhanced CaMV35S promoter.

Results of reproductive evaluations are shown in FIG. 11. These calculations are based upon a numerical scoring system relative to nonsprayed controls. Reproductive scores are examined at 28 days after spraying and are based upon six distinct conditions in which the main meristem or flowers reacted to the glyphosate. The scale used is:

0 = no floral bud development
2 = floral buds, but aborted prior to opening
4 = flowers without anthers, anthers should protrude past petals
6 = flowers with normal appearing anthers, but sterile
8 = flowers with partially sterile anthers
10 = fully fertile flowers FIG. 11 compares the reproductive scores of the total number of transgenic canola lines containing the meristematic promoter from *Arabidopsis thaliana* with three transgenic lines containing only the enhanced CaMV35S promoter. As is shown in FIG. 11, the plants transformed with the promoter of the present invention exhibit increased expression of resistant enzyme in the vegetative meristematic region of the plant by having higher reproductive scores in glyphosate spray tests than those of plants containing only the enhanced CaMV35S promoter. The transgenic lines that show reproductive scores of 0 or 2 are believed to be "escapes" where the chimeric gene is not being expressed, possibly as a result of incomplete transformation.

These results demonstrate an improved tolerance to glyphosate through expression of the genomic clone of the variant *Arabidopsis thaliana* EPSP synthase directed by the *A. thaliana* meristematic promoter.

Example 21

Figure 12:
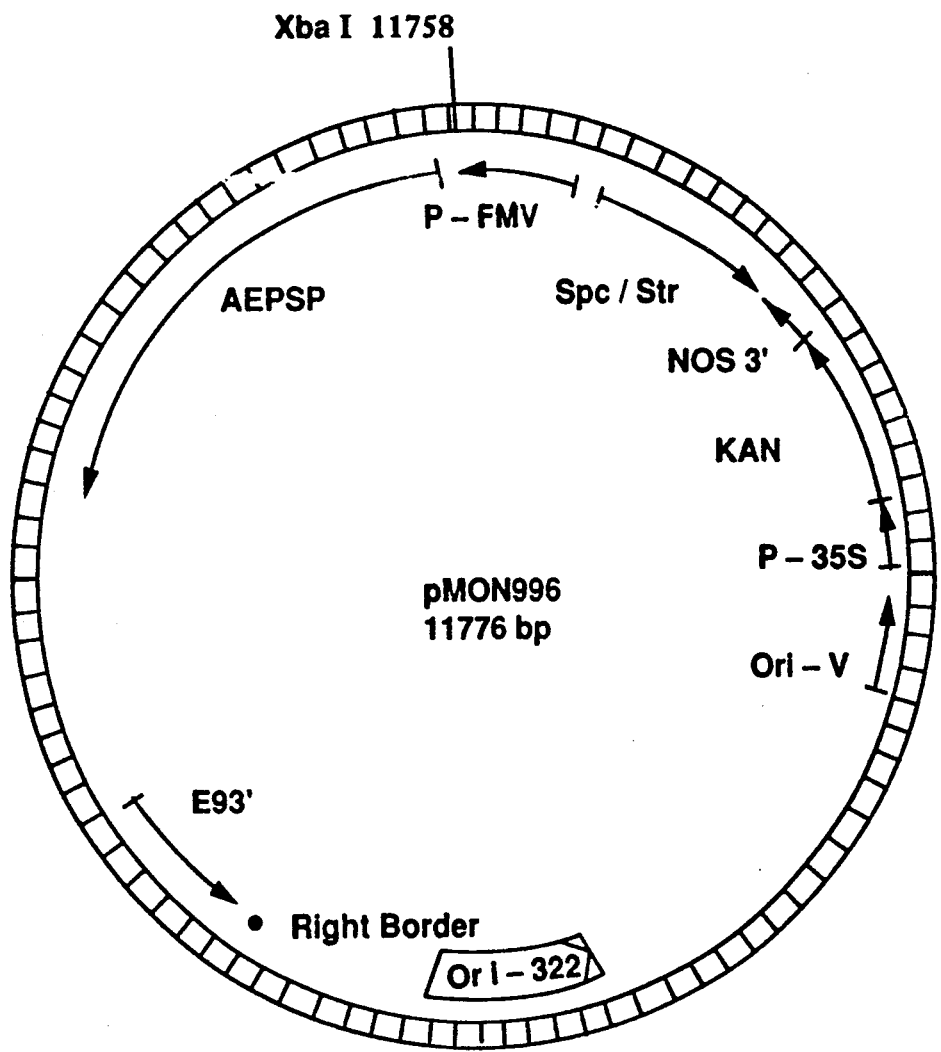
FIG. 12 shows a physical map of pMON996.
Figure 13:
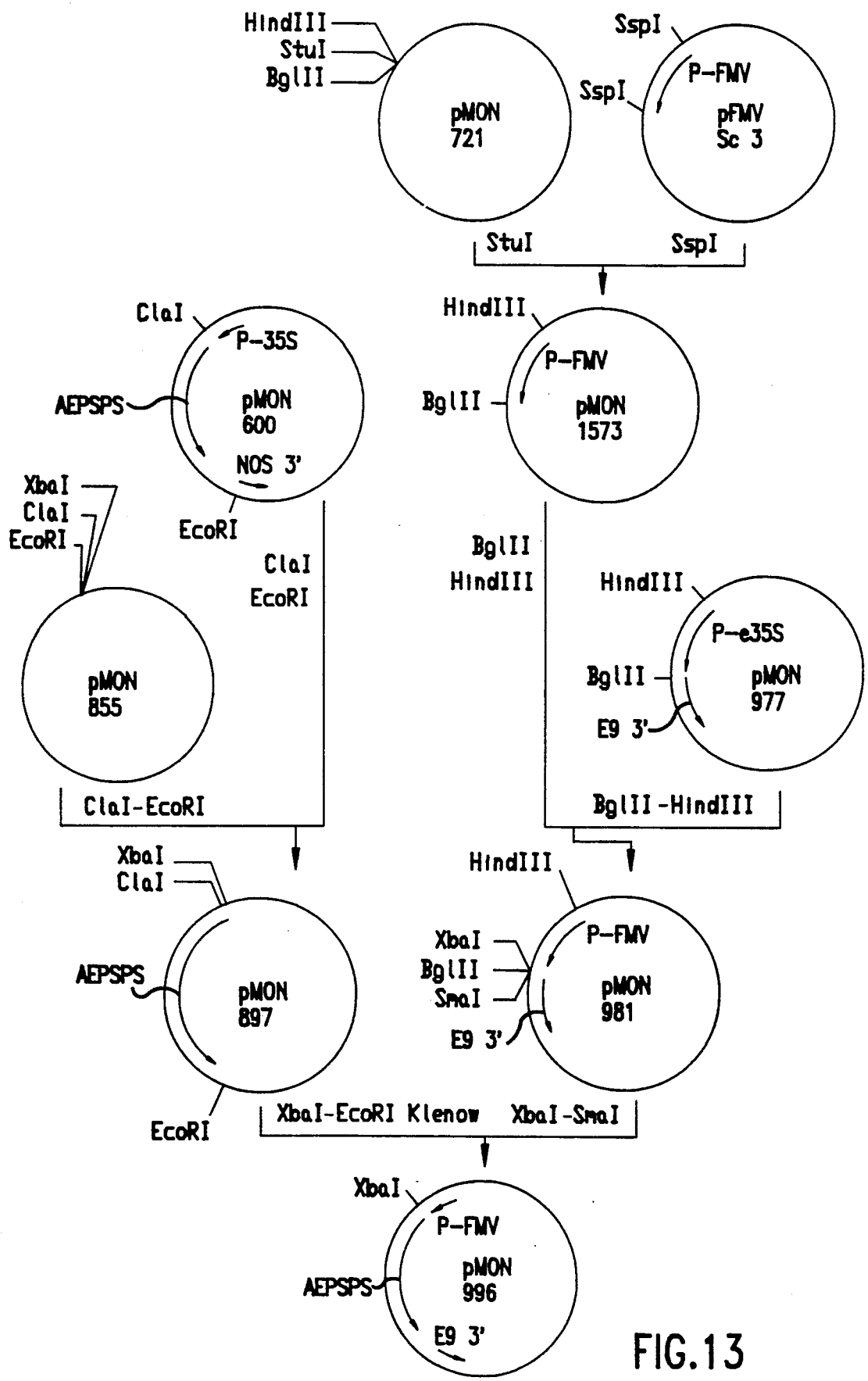
FIG. 13 shows the steps employed in the preparation of pMON996.

Transgenic plants containing the Arabidopsis EPSP synthase gene containing a single glycine to alamine mutation at nucleotide 101 driven by either the FMV promoter or the CaMVe35S promoter were obtained and analyzed for resistance to glyphosate. The transgenic plants containing the Arabidopsis EPSP synthase gene (as described above) directed by the FMV promoter contained pMON996, FIG. 12 and FIG. 13, while those plants containing the enhanced CaMVe35S promoter contained pMON899. These transgenic plants were planted and the seed from the R$_o$ plants harvested, threshed and dried before planting for a glyphosate spray test. The progeny were planted in 4-inch square pots of Metro 350 and three types of slow release fertilizers. A goal of twenty seedlings from each R$_o$ plant is desirable for testing. Germination frequency is usually high but overplanting ensures that twenty seedlings are present. The plants were thinned down by selecting the twenty most vigorous and erect seedlings seven to ten days after planting. A negative control (non-transformed, "Westar" variety) was planted at the same time to maintain quality and display the results. The plants were maintained and grown in a greenhouse environment. A sixteen-hour photoperiod and a temperature of 21° C. (day) and 15° C. (night) was maintained. Water soluble Peters Pete Lite fertilizer with an analysis of 20-19-18 was applied once per week or as needed.

Two plants from each R$_o$ progeny were not sprayed and served as controls to compare and measure the glyphosate tolerance. When the remaining plants reached the six to eight leaf stage, usually 20 to 28 days after planting, glyphosate was applied at a rate equivalent to 0.28 Kg/ha. Low rate technology using low volumes has been adopted. A volume of ten imperial gallons for 0.28 Kg/ha of glyphosate is standard in field tests. A laboratory test sprayer had been calibrated to deliver a consistent rate equivalent to field conditions.

Figure 14:
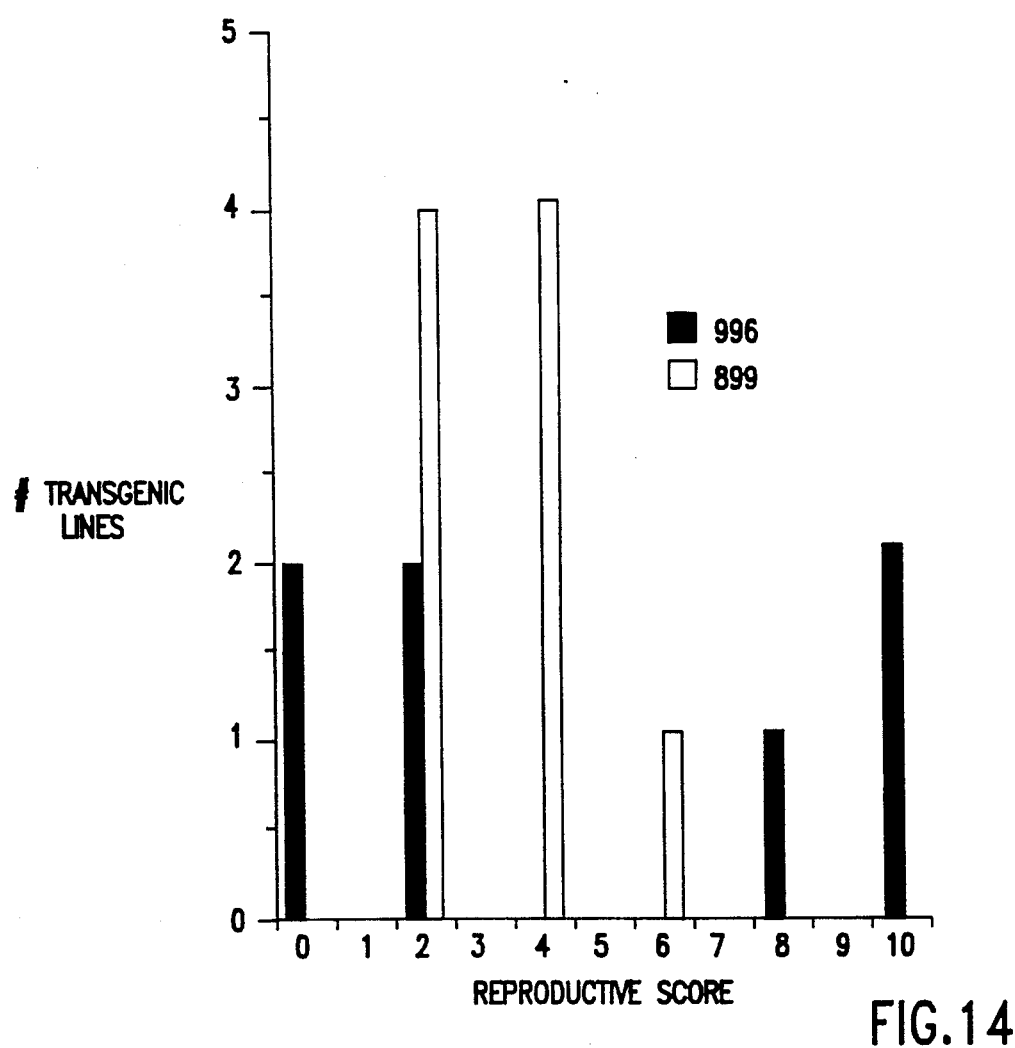
FIG. 14 shows the reproductive scores of transgenic plants containing mutant EPSPS under the control of the FMV full-length transcript promoter (pMON996) or CaMVe35S promoter (pMON899) after glyphosate application.

Results of reproductive evaluations are shown in FIG. 14. These calculations are based upon a numerical scoring system relative to nonsprayed controls. Reproductive scores are examined at 28 days after spraying and are based upon six distinct conditions in which the main meristem or flowers reacted to the glyphosate. The scale used is:

0 = no floral bud development
2 = floral buds, but aborted prior to opening
4 = flowers without anthers, anthers should protrude past petals
6 = flowers with normal appearing anthers, but sterile
8 = flowers with partially sterile anthers
10 = fully fertile flowers FIG. 14 compares the reproductive scores of the total number of transgenic canola lines containing the FMV promoter with transgenic lines containing the CaMVe35S promoter. As can be seen in FIG. 14, the reproductive scores of three of the seven transgenic lines containing the FMV promoter (pMON996) are better than any of the scores from lines containing the CaMVe35S promoter (pMON899). In fact, the transgenic lines containing pMON899 used in FIG. 14 exhibit the highest levels of glyphosate tolerance among 150 lines previously tested. This demonstrates that the FMV promoter more uniformly expresses a gene product throughout the tissues and cells of the plant, and particularly in the floral buds. It is to be understood that an increased level of expression in the floral buds is important for maximal glyphosate resistance.

The embodiments and examples described above are provided to better elucidate the practice of the present invention. It should be understood that these embodiments and examples are provided for illustrative purposes only, and are not intended to limit the scope of the invention.

REFERENCES

Adams, S. P. et al. (1983) *J. Amer. Chem. Soc.* 105: 661

Amrhein, N. et al. (1980) *Naturwissenschafter* 67: 356-357.

Arnon, D. I. (1949) Plant Physiol. 24,1-15

Ausubel, F. et al (1980) *Plant Mol. Bio. Newsletter* 1: 26-32.

Barinaga, M. R. et al. (1981) "Methods for the Transfer of DNA, RNA and Protein to Nitrocellulose and Diazotized Paper Solid Supports", pub. by Schleicher and Schuell Inc., Keene N.H.

Bartlett, S. G., Grossman, A. R. & Chua N. H. (1982) in *Methods in Chloroplast Molecular Biology*, Elsevier Biomedical Press, New York, pp 1081-1091.

Bevan, M. et al. (1983) *Nature* 304: 184.

Broglie, R. et al. (1983) *Bio/Technology* 1: 55-61.

Comai, L. et al. (1983) *Science* 221: 370-371.

Davis, R. W. et al. (1980) *Advanced Bacterial Genetics*, Cold Spring Harbor Labs, NY.

DeCleene, M. and DeLey, J. (1976) Bot. Review 42: 389-466.

DePicker, A. et al. (1982) *J. Mol. Appl. Gen.* 1: 561.

Ditta, G. et al (1980) *Pro. Natl. Acad. Sci. U.S.A.* 77:7347

Edelman, M., Hallick, R. B. & Chua, N. H. (Elsevier Biomedical Press, New York), pp. 1081-1091.

Fraley, R. T. et al. (1983) *Proc. Natl. Acad. Sci. U.S.A.* 80: 4803.

Goldberg, R. B. et al., (1981) *Devel. Bio.* 83: 201-217.

Hernalsteens, J. P. et al. (1985), EMBO Journal 3: 3039-3041.

Herrera-Estrella, L. et al. (1983) *Nature* 303: 209 Hooykaas-Van Slogteren, G. M. S. et al. (1984) *Nature* 311: 763-764.

Horsch, R. B. and Jones, G. E. (1980) *In Vitro* 16: 103-108.

Horsch, R. B. et al. (1985) *Science* 227: 1229-1231.

Horsch, R. B. and Klee, H. J. (1986) *Proc. Natl. Acad. Sci. U.S.A.* 83, 4428-4432.

Hunkapiller, M. W. et al. (1983a) *Methods Enzymol.* 91: 399-413.

Hunkapiller, M. W. et al. (1983b) *Methods Enzymol.* 91: 486-493.

Huynh, T. V. et al, (1985) in *DNA Cloning Techniques: A Practical Approach*, D. Glover (ed.), IRL Press, Oxford, England Krieg, P. A. & Melton, D. A. (1984) Nucleic Acids Res. 12; 7057-7070.

Laemmli, U. K. (1970) Nature 227, 680-685.

Lizardi, P. M. (1982) "Binding and Recovery of DNA and RNA using NA-45 DEAE Membrane." Schleicher and Schuell, Inc., Keene, N.H.

Maniatis, T. et al. (1982) *Molecular Cloning: A Laboratory Manual*, Cold Spring Harbor Labs, NY.

Maxam, A. M. and W. Gilbert (1977) *P.N.A.S. U.S.A.* 74: 560-564.

Meagher, R. B. et al. (1977) *Virology* 80: 362-375.

Messing, J. et al. (1981). *Nucleic Res.* 9: 309-321.

Messing, J. and J. Vieira (1982), *Gene* 19: 69-276.

Mousdale, D. M. and Coggins, J. R. (1984) *Planta* 160: 78-83.

Nafziger, E. D., et al (1984), *Plant Physiol*, 76, 571.

Mousdale, D. M. and Coggins, J. R. (1985) *Planta* 163: 241-294.

Rogers, S. G. et al. (1983) *Appl. Envir. Microbio.* 46: 37-43.

Rubin, J. et al. (1982) *Plant Phys.* 70: 833-839.

Scherer, et al. (1981) *Development Bio.* 86: 438-447.

Schimke, R. T., ed. (1982) *Gene Amplification*, Cold Spring Harbor Labs.

Smart, C. C., et al (1985), *J. Biol. Chem.* 30, 16338.

Southern, E. M. (1975) *J. Mol. Biol.* 98: 503–517.
Stalker, D. M. et al. (1985) *J. Biol. Chem.* 260: 4724–4728.
Steinrucken, H. and Amrhein, N. (1980) *Biochem. & Biophys. Res. Comm.* 94: 1207–1212.
Vieira, J. et al. (1982), *Gene* 19: 259–268.
Steinrucken, H. et al. (1985) *Arch. Biochem. Biophys.* (in press).
Young, R. A. and R. W. Davis. (1983), *Proc. Natl. Acad. Sci., U.S.A.* 80: 1194–1198.
Zoller, M. M. et al, (1983), *Methods Enzymol.*, 100, 468.

What is claimed is:

1. A method for selectively controlling weeds in a field containing a crop of planted crop seeds or plants which method comprises the steps of:
    a) planting said crop seeds or plants which are glyphosate resistant as a result of a chimeric gene being inserted into said crop seed or plant, said chimeric gene having
        i) a promoter sequence which functions in plant cells,
        ii) a coding sequence which causes the production of RNA, encoding a chloroplast transit peptide/5-enolpyruvylshikimate-3-phosphate synthase fusion polypeptide, which chloroplast transit peptide permits the fusion polypeptide to be imported into a chloroplast of a plant cell, and
        iii) a 3' non-translated region which encodes a polyadenylation signal which functions in plant cells to cause the addition of polyadenylate nucleotides to the 3' end of the RNA,
        where the promoter is heterologous with respect to the coding sequence and adapted to cause sufficient expression of the fusion polypeptide to enhance the glyphosate resistance of a plant cell transformed with said gene; and
    b) applying to said crop and weeds in said field a sufficient amount of glyphosate to control said weeds without significantly affecting said crop.

2. The method of claim 1 wherein said promoter sequence is a plant virus promoter sequence.

3. The method of claim 2 wherein said promoter sequence is a promoter sequence from cauliflower mosaic virus (CaMV).

4. The method of claim 3 wherein said promoter sequence is the CaMV35S promoter sequence.

5. The method of claim 1 in which the coding sequence encodes a glyphosate-tolerant 5-enolpyruvylshikimate-3-phosphate synthase (EPSPS).

6. The method of claim 1 in which the EPSPS coding sequence encodes an EPSPS from an organism selected from the group consisting of bacteria, fungi and plants.

7. The method of claim 1 wherein said chloroplast transit peptide is from a plant EPSPS gene.

8. A glyphosate-resistant dicotyledonous plant seed, said seed comprising a chimeric plant gene having:
    i) a promoter sequence which functions in plant cells;
    ii) a coding sequence which causes the production of RNA, encoding a chloroplast transit peptide/5-enolpyruvylshikimate-3-phosphate synthase fusion polypeptide, which chloroplast transit peptide permits the fusion polypeptide to be imported into a chloroplast of a plant cell; and
    iii) a 3' non-translated region which encodes a polyadenylation signal which functions in plant cells to cause the addition of polyadenylate nucleotides to the 3' end of the RNA,
    where the promoter is heterologous with respect to the coding sequence and adapted to cause sufficient expression of the fusion polypeptide to enhance the glyphosate resistance of a plant cell transformed with said gene.

9. The glyphosate-resistant dicotyledonous plant seed of claim 8 wherein said promoter sequence is a plant virus promoter sequence.

10. The glyphosate-resistant dicotyledonous plant seed of claim 9 wherein said promoter sequence is a promoter sequence from cauliflower mosaic virus (CaMV).

11. The glyphosate-resistant dicotyledonous plant seed of claim 10 wherein said promoter sequence is the CaMV35S promoter sequence.

12. The glyphosate-resistant dicotyledonous plant seed of claim 8 wherein said coding sequence encodes a mutant 5-enolpyruvylshikimate-3-phosphate synthase.

13. The glyphosate-resistant dicotyledonous plant seed of claim 8 wherein said coding sequence encodes an EPSPS from an organism selected from the group consisting of bacteria, fungi and plants.

14. The glyphosate-resistant dicotyledonous plant seed of claim 8 wherein said chloroplast transit peptide is from a plant EPSPS gene.

15. A glyphosate-resistant tomato seed of claim 8.
16. A glyphosate-resistant tobacco seed of claim 8.
17. A glyphosate-resistant oil seed rape seed of claim 8.
18. A glyphosate-resistant flax seed of claim 8.
19. A glyphosate-resistant soybean seed of claim 8.
20. A glyphosate-resistant sunflower seed of claim 8.
21. A glyphosate-resistant sugar beet seed of claim 8.
22. A glyphosate-resistant alfalfa seed of claim 8.
23. A glyphosate-resistant cotton seed of claim 8.

* * * * *